US012767643B2

(12) United States Patent
Chan et al.

(10) Patent No.: US 12,767,643 B2

(45) Date of Patent: Oct. 20, 2026

(54) HYDROLYSIS-RESISTANT ESTERS FOR DRUG AND IMAGING AGENT DELIVERY

(71) Applicant: The Board of Trustees of the University of Illinois, Urbana, IL (US)

(72) Inventors: Jefferson Kar Fai Chan, Savoy, IL (US); Anuj K. Yadav, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 316 days.

(21) Appl. No.: 18/498,933

(22) Filed: Oct. 31, 2023

(65) Prior Publication Data

US 2024/0158359 A1 May 16, 2024

Related U.S. Application Data

(60) Provisional application No. 63/420,787, filed on Oct. 31, 2022.

(51) Int. Cl.

| | |
|---|---|
| ***C07D 277/10*** | (2006.01) |
| ***A61K 31/40*** | (2006.01) |
| ***A61K 31/525*** | (2006.01) |
| ***A61P 31/00*** | (2006.01) |

(52) U.S. Cl.

CPC ............ *C07D 277/10* (2013.01); *A61K 31/40* (2013.01); *A61K 31/525* (2013.01); *A61P 31/00* (2018.01)

(58) Field of Classification Search

None

See application file for complete search history.

(56) References Cited

U.S. PATENT DOCUMENTS

| | | | |
|---|---|---|---|
| 9,341,630 | B2 | 5/2016 | Shabat |
| 10,751,423 | B2 | 8/2020 | Ghoroghchian |
| 2020/0338211 | A1 | 10/2020 | Sau |

OTHER PUBLICATIONS

Muz, B.; de la Puente, P.; Azab, F.; Azab, A. K. The Role of Hypoxia in Cancer Progression, Angiogenesis, Metastasis, and Resistance to Therapy. Hypoxia 2015, 83. https://doi.org/10.2147/HP.S93413.

O'Sullivan, J. J.; Heffern, M. C. Development of an ATP-Independent Bioluminescent Probe for Detection of Extracellular Hydrogen Peroxide. Org. Biomol. Chem. 2022, 20 (31), 6231-6238. https://doi.org/10.1039/D2OB00436D.

O'Sullivan, J. J.; Medici, V.; Heffern, M. C. A Caged Imidazopyrazinone for Selective Bioluminescence Detection of Labile Extracellular Copper( <scp>ii</Scp> ). Chem. Sci. 2022, 13 (15), 4352-4363. https://doi.org/10.1039/D1SC07177G.

Pino, N. W.; Davis, J.; Yu, Z.; Chan, J. NitroxylFluor: A Thiol-Based Fluorescent Probe for Live-Cell Imaging of Nitroxyl. J. Am. Chem. Soc. 2017, 139 (51), 18476-18479. https://doi.org/10.1021/jacs.7b11471.

Porterfield, W. B.; Jones, K. A.; McCutcheon, D. C.; Prescher, J. A. A "Caged" Luciferin for Imaging Cell-Cell Contacts. J. Am. Chem. Soc. 2015, 137 (27), 8656-8659. https://doi.org/10.1021/jacs.5b02774.

Qin, W.; Xu, C.; Zhao, Y.; Yu, C.; Shen, S.; Li, L.; Huang, W. Recent Progress in Small Molecule Fluorescent Probes for Nitroreductase. Chinese Chem. Lett. 2018, 29 (10), 1451-1455. https://doi.org/10.1016/j.cclet.2018.04.007.

Rakotomalala, A.; Escande, A.; Furlan, A.; Meignan, S.; Lartigau, E. Hypoxia in Solid Tumors: How Low Oxygenation Impacts the "Six Rs" of Radiotherapy. Front. Endocrinol. (Lausanne). 2021, 12. https://doi.org/10.3389/fendo.2021.742215.

Rathbun, C. M.; Prescher, J. A. Bioluminescent Probes for Imaging Biology beyond the Culture Dish. Biochemistry 2017, 56 (39), 5178-5184. https://doi.org/10.1021/acs.biochem.7b00435.

Ressler, V. T.; Mix, K. A.; Raines, R. T. Esterification Delivers a Functional Enzyme into a Human Cell. ACS Chem. Biol. 2019, 14 (4), 599-602. https://doi.org/10.1021/acschembio.9b00033.

Sellmyer, M. A.; Bronsart, L.; Imoto, H.; Contag, C. H.; Wandless, T. J.; Prescher, J. A. Visualizing Cellular Interactions with a Generalized Proximity Reporter. Proc. Natl. Acad. Sci 2013, 110 (21), 8567-8572. https://doi.org/10.1073/pnas.1218336110.

Su, T. A.; Bruemmer, K. J.; Chang, C. J. Caged Luciferins for Bioluminescent Activity-Based Sensing. Curr. Opin. Biotechnol. 2019, 60, 198-204. https://doi.org/10.1016/j.copbio.2019.05.002.

Tian, X.; Li, Z.; Lau, C.; Lu, J. Visualization of in Vivo Hydrogen Sulfide Production by a Bioluminescence Probe in Cancer Cells and Nude Mice. Anal. Chem. 2015, 87 (22), 11325-11331. https://doi.org/10.1021/acs.analchem.5b03712.

Ticho, A. L.; Lee, H.; Gill, R. K.; Dudeja, P. K.; Saksena, S.; Lee, D.; Alrefai, W. A. A Novel Bioluminescence-Based Method to Investigate Uptake of Bile Acids in Living Cells. Am. J. Physiol. Liver Physiol. 2018, 315 (4), G529-G537. https://doi.org/10.1152/ajpgi.00133.2018.

Tran, D. N.; Battilocchio, C.; Lou, S.-B.; Hawkins, J. M.; Ley, S. V. Flow Chemistry as a Discovery Tool to Access Sp 2-Sp 3 Cross-Coupling Reactions via Diazo Compounds. Chem. Sci. 2015, 6 (2), 1120-1125. https://doi.org/10.1039/C4SC03072A.

Tsakos, M.; Schaffert, E. S.; Clement, L. L.; Villadsen, N. L.; Poulsen, T. B. Ester Coupling Reactions—an Enduring Challenge in the Chemical Synthesis of Bioactive Natural Products. Nat. Prod. Rep. 2015, 32 (4), 605-632. https://doi.org/10.1039/C4NP00106K.

Tsien, R. Y. New Calcium Indicators and Buffers with High Selectivity against Magnesium and Protons: Design, Synthesis, and Properties of Prototype Structures. Biochemistry 1980, 19 (11), 2396-2404. https://doi.org/10.1021/bi00552a018.

(Continued)

*Primary Examiner* — Adam C Milligan

*Assistant Examiner* — Brianna L Bauer

(74) *Attorney, Agent, or Firm* — Dilworth IP, LLC

(57) ABSTRACT

A novel carboxylate luciferin substrate or methotrexate compound is disclosed as having at least one substituted benzyl ester group masking a carboxyl group. The substituted benzyl ester group may have a stabilizing substitution on the benzylic position. The stabilizing substitution on the benzylic position may be a methyl, phenyl group or a branched $C_3$-$C_5$ alkyl group. The luciferin substrate may provide an imaging agent or ABS may have NIR BL activity. Optionally, there is a trigger group at the para position or ortho position, or optionally both.

5 Claims, 15 Drawing Sheets

(11 of 15 Drawing Sheet(s) Filed in Color)

(56) References Cited

OTHER PUBLICATIONS

Van de Bittner, G. C.; Bertozzi, C. R.; Chang, C. J. Strategy for Dual-Analyte Luciferin Imaging: In Vivo Bioluminescence Detection of Hydrogen Peroxide and Caspase Activity in a Murine Model of Acute Inflammation. J. Am. Chem. Soc. 2013, 135 (5), 1783-1795 https://doi.org/10.1021/ja309078t.
Van de Bittner, G. C.; Dubikovskaya, E. A.; Bertozzi, C. R.; Chang, C. J. In Vivo Imaging of Hydrogen Peroxide Production in a Murine Tumor Model with a Chemoselective Bioluminescent Reporter. Proc. Natl. Acad. Sci. 2010, 107 (50), 21316-21321. https://doi.org/10.1073/pnas.1012864107.
Vieira, J.; Pinto da Silva, L.; Esteves da Silva, J. C. G. Advances in the Knowledge of Light Emission by Firefly Luciferin and Oxyluciferin. J. Photochem. Photobiol. B Biol. 2012, 117, 33-39. https://doi.org/10.1016/j.jphotobiol.2012.08.017.
Vorobyeva, A. G.; Stanton, M.; Godinat, A.; Lund, K. B.; Karateev, G. G.; Francis, K. P.; Allen, E.; Gelovani, J. G.; McCormack, E.; Tangney, M.; Dubikovskaya, E. A. Development of a Bioluminescent Nitroreductase Probe for Preclinical Imaging. PLoS One 2015, 10 (6), e0131037.https://doi.org/10.1371/journal.pone.0131037.
Wang, D.-D.; Jin, Q.; Zou, L.-W.; Hou, J.; Lv, X.; Lei, W.; Cheng, H.-L.; Ge, G.-B.; Yang, L. A Bioluminescent Sensor for Highly Selective and Sensitive Detection of Human Carboxylesterase 1 in Complex Biological Samples. Chem. Commun. 2016, 52 (15), 3183-3186. https://doi.org/10.1039/C5CC09874B.
Wang, D.-D.; Zou, L.-W.; Jin, Q.; Guan, X.-Q.; Yu, Y.; Zhu, Y.-D.; Huang, J.; Gao, P.; Wang, P.; Ge, G.-B.; Yang, L. Bioluminescent Sensor Reveals That Carboxylesterase 1A Is a Novel Endoplasmic Reticulum-Derived Serologic Indicator for Hepatocyte Injury. ACS Sensors 2020, 5(7), 1987-1995. https://doi.org/10.1021/acssensors.0c00384.
Wender, P. A.; Goun, E. A.; Jones, L. R.; Pillow, T. H.; Rothbard, J. B.; Shinde, R.; Contag, C. H. Real-Time Analysis of Uptake and Bioactivatable Cleavage of Luciferin-Transporter Conjugates in Transgenic Reporter Mice. Proc. Natl. Acad. Sci. 2007, 104 (25), 10340-10345. https://doi.org/10.1073/pnas.0703919104.
Wong, R. H. F.; Kwong, T.; Yau, K.-H.; Au-Yeung, H. Y. Real Time Detection of Live Microbes Using a Highly Sensitive Bioluminescent Nitroreductase Probe. Chem. Commun. 2015, (21), 4440-4442. https://doi.org/10.1039/C4CC10345A.
Yadav, A. K.; Hernandez, S.; Su, S.; Chan, J. Acoustic-Based Chemical Tools for Profiling the Tumor Microenvironment. Curr. Opin. Chem. Biol. 2020, 57, 114-121. https://doi.org/10.1016/j.cbpa.2020.06.008.
Yadav, A. K.; Lee, M. C.; Lucero, M. Y.; Su, S.; Reinhardt, C. J.; Chan, J. Activity-Based NIR Bioluminescence Probe Enables Discovery of Diet-Induced Modulation of the Tumor Microenvironment via Nitric Oxide. ACS Cent. Sci. 2022, 8 (4), 461-472. https://doi.org/10.1021/acscentsci.1c00317.
Yan, J.; Lee, S.; Zhang, A.; Yoon, J. Self-Immolative Colorimetric, Fluorescent and Chemiluminescent Chemosensors. Chem. Soc. Rev. 2018, 47 (18), 6900-6916. https://doi.org/10.1039/C7CS00841D.
Yang, K.; Leslie, K. G.; Kim, S. Y.; Kalionis, B.; Chrzanowski, W.; Jolliffe, K. A.; New, E. J Tailoring the Properties of a Hypoxia-Responsive 1,8-Naphthalimide for Imaging Applications. Org. Biomol. Chem. 2018, 16 (4), 619-624. https://doi.org/10.1039/C7OB03164E.
Yang, N. J.; Hinner, M. J. Getting Across the Cell Membrane: An Overview for Small Molecules, Peptides, and Proteins BT—Site-Specific Protein Labeling: Methods and Protocols; Gautier, A., Hinner, M. J., Eds.; Springer New York: New York, NY, 2015; pp. 29-53. https://doi.org/10.1007/978-1-4939-2272-7_3.
Yao, H.; So, M.; Rao, J. A Bioluminogenic Substrate for In Vivo Imaging of β-Lactamase Activity. Angew. Chemie Int. Ed. 2007, 46 (37), 7031-7034. https://doi.org/10.1002/anie.200701931.
Zhou, W.; Shultz, J. W.; Murphy, N.; Hawkins, E. M.; Bernad, L.; Good, T.; Moothart, L.; Frackman, S.; Klaubert, D. H.; Bulleit, R. F.; Wood, K. V. Electrophilic Aromatic Substituted Luciferins as Bioluminescent Probes for Glutathione S-Transferase Assays. Chem. Commun. 2006, No. 44, 4620. https://doi.org/10.1039/b610682j.
Aron, A. T.; Heffern, M. C.; Lonergan, Z. R.; Vander Wal, M. N.; Blank, B. R.; Spangler, B.; Zhang, Y.; Park, H. M.; Stahl, A.; Renslo, A. R.; Skaar, E. P.; Chang, C. J. In Vivo Bioluminescence Imaging of Labile Iron Accumulation in a Murine Model of Acinetobacter Baumannii Infection. Proc. Natl. Acad. Sci. 2017, 114 (48), 12669-12674. https://doi.org/10.1073/pnas.1708747114.
Beaumont, K.; Webster, R.; Gardner, I.; Dack, K. Design of Ester Prodrugs to Enhance Oral Absorption of Poorly Permeable Compounds: Challenges to the Discovery Scientist. Curr. Drug Metab. 2003, 4 (6), 461-485. https://doi.org/10.2174/1389200033489253.
Bender, M. L.; Turnquest, B. W. General Basic Catalysis of Ester Hydrolysis and Its Relationship to Enzymatic Hydrolysis 1. J. Am. Chem. Soc. 1957, 79 (7), 1656-1662. https://doi.org/10.1021/ja01564a035.
Bruemmer, K. J.; Crossley, S. W. M.; Chang, C. J. Activity-Based Sensing: A Synthetic Methods Approach for Selective Molecular Imaging and Beyond. Angew. Chemie Int. Ed. 2020, 59 (33), 13734-13762. https://doi.org/10.1002/anie.201909690.
Cao, J.; Campbell, J.; Liu, L.; Mason, R. P.; Lippert, A. R. In Vivo Chemiluminescent Imaging Agents for Nitroreductase and Tissue Oxygenation. Anal. Chem. 2016, 88 (9), 4995-5002. https://doi.org/10.1021/acs.analchem.6b01096.
Carl, P. L.; Chakravarty, P. K.; Katzenellenbogen, J. A. A Novel Connector Linkage Applicable in Prodrug Design. J. Med. Chem. 1981, 24 (5), 479-480. https://doi.org/10.1021/jm00137a001.
Chan, J.; Dodani, S. C.; Chang, C. J. Reaction-Based Small-Molecule Fluorescent Probes for Chemoselective Bioimaging. Nat. Chem. 2012, 4 (12), 973-984. https://doi.org/10.1038/nchem.1500.
Chen, W.; Liu, C.; Peng, B.; Zhao, Y.; Pacheco, A.; Xian, M. New Fluorescent Probes for Sulfane Sulfurs and the Application in Bioimaging. Chem. Sci. 2013, 4 (7), 2892. https://doi.org/10.1039/c3sc50754h.
Choi, M. G.; Hwang, J.; Eor, S.; Chang, S.-K. Chromogenic and Fluorogenic Signaling of Sulfite by Selective Deprotection of Resorufin Levulinate. Org. Lett. 2010, 12 (24), 5624-5627. https://doi.org/10.1021/ol102298b.
Cohen, A. S.; Dubikovskaya, E. A.; Rush, J. S.; Bertozzi, C. R. Real-Time Bioluminescence Imaging of Glycans on Live Cells. J. Am. Chem. Soc. 2010, 132 (25), 8563-8565. https://doi.org/10.1021/ja101766r.
Denny, W. A. Nitroaromatic Hypoxia-Activated Prodrugs for Cancer Therapy. Pharmaceuticals 2022, 15 (2), 187. https://doi.org/10.3390/ph15020187.
Dragulescu-Andrasi, A.; Liang, G.; Rao, J. In Vivo Bioluminescence Imaging of Furin Activity in Breast Cancer Cells Using Bioluminogenic Substrates. Bioconjug. Chem. 2009, 20 (8), 1660-1666. https://doi.org/10.1021/bc9002508.
East, A. K.; Lucero, M. Y.; Chan, J. New Directions of Activity-Based Sensing for in Vivo NIR Imaging. Chem. Sci. 2021, 12 (10), 3393-3405. https://doi.org/10.1039/D0SC03096A.
Endo, M.; Ozawa, T. Advanced Bioluminescence System for In Vivo Imaging with Brighter and Red-Shifted Light Emission. Int. J. Mol. Sci. 2020, 21 (18), 6538. https://doi.org/10.3390/ijms21186538.
Evans, M. S.; Chaurette, J. P.; Adams, S. T.; Reddy, G. R.; Paley, M. A.; Aronin, N.; Prescher, J. A.; Miller, S. C. A Synthetic Luciferin Improves Bioluminescence Imaging in Live Mice. Nat. Methods 2014, 11 (4), 393-395. https://doi.org/10.1038/nmeth.2839.
Fife, T. H.; Przystas, T. J. Divalent Metal Ion Catalysis in the Hydrolysis of Esters of Picolinic Acid. Metal Ion Promoted Hydroxide Ion and Water Catalyzed Reactions. J. Am. Chem. Soc. 1985, 107 (4), 1041-1047. https://doi.org/10.1021/ja00290a048.
Forsdahl, G.; Erceg, D.; Geisendorfer, T.; Turkalj, M.; Plavec, D.; Thevis, M.; Tretzel, L.; Gmeiner, G. Detection of Testosterone Esters in Blood. Drug Test. Anal. 2015, 7 (11-12), 983-989, https://doi.org/10.1002/dta.1914.
Gardner, S. H.; Brady, C. J.; Keeton, C.; Yadav, A. K.; Mallojala, S. C.; Lucero, M. Y.; Su, S.; Yu, Z.; Hirschi, J. S.; Mirica, L. M.; Chan, J. A General Approach to Convert Hemicyanine Dyes Into Highly

(56) References Cited

OTHER PUBLICATIONS

Optimized Photoacoustic Scaffolds for Analyte Sensing**. Angew. Chemie Int. Ed. 2021, 60( 34), 18860-18866. https://doi.org/10.1002/anie.202105905.
Gardner, S. H.; Reinhardt, C. J.; Chan, J. Advances in Activity-Based Sensing Probes for Isoform-Selective Imaging of Enzymatic Activity. Angew. Chemie Int. Ed. 2021, 60 (10), 5000-5009, https://doi.org/10.1002/anie.202003687.
Geiger, R.; Schneider, E.; Wallenfels, K.; Miska, W. A New Ultrasensitive Bioluminogenic Enzyme Substrate for 6-Galactosidase. Biol. Chem. Hoppe. Seyler. 1992, 373 (2), 1187-1192. https://doi.org/10.1515/bchm3.1992.373.2.1187.
Hall, M. P.; Woodroofe, C. C.; Wood, M. G.; Que, I.; van't Root, M.; Ridwan, Y.; Shi, C.; Kirkland, T. A.; Encell, L. P.; Wood, K. V.; Löwik, C.; Mezzanotte, L. Click Beetle Luciferase Mutant and near Infrared Naphthyl-Luciferins for Improved Bioluminescence Imaging. Nat. Commun. 2018, 9 (1), 132. https://doi.org/10.1038/s41467-017-02542-9.
Heffern, M. C.; Park, H. M.; Au-Yeung, H. Y.; Van de Bittner, G. C.; Ackerman, C. M.; Stahl, A.; Chang, C. J. In Vivo Bioluminescence Imaging Reveals Copper Deficiency in a Murine Model of Nonalcoholic Fatty Liver Disease. Proc. Natl. Acad. Sci. 2016, 113 (50), 14219-14224. https://doi.org/10.1073/pnas.1613628113.
Henkin, A. H.; Cohen, A. S.; Dubikovskaya, E. A.; Park, H. M.; Nikitin, G. F.; Auzias, M. G.; Kazantzis, M.; Bertozzi, C. R.; Stahl, A. Real-Time Noninvasive Imaging of Fatty Acid Uptake in Vivo. ACS Chem. Biol. 2012, 7 (11), 1884-1891. https://doi.org/10.1021/cb300194b.
Hou, Y.; Yang, X.-F.; Zhong, Y.; Li,Z. Development of Fluorescent Probes for Hydrogen polysulfides bu Using Cinnamate Ester as the Reacognition Unit. Sensors Actuators B Chem. 2016, 232, 531-537. https://doi.org/10.1016/j.snb.2016.04.008.
Hu, S.; Wang, J.; Luo, M.; Wu, Z.; Hou, Y.; Chen, X. A Novel ESIPT Fluorescent Probe Derived from 3-Hydroxyphthalimide for Hydrazine Detection in Aqueous Solution and Living Cells. Anal. Bioanal. Chem. 2021, 413 (21), 5463-5468. https://doi.org/10.1007/s00216-021- 03530-1.
Kailass, K.; Sadovski, O.; Capello, M.; Kang, Y.; Fleming, J. B.; Hanash, S. M.; Beharry, A. A. Measuring Human Carboxylesterase 2 Activity in Pancreatic Cancer Patient-Derived Xenografts Using a Ratiometric Fluorescent Chemosensor. Chem. Sci. 2019, 10 (36), 8428-8437. https://doi.org/10.1039/C9SC00283A.
Kaskova, Z. M.; Tsarkova, A. S.; Yampolsky, I. V. 1001 Lights: Luciferins, Luciferases, Their Mechanisms of Action and Applications in Chemical Analysis, Biology and Medicine. Chem. Soc. Rev.2016, 45 (21), 6048-6077. https://doi.org/10.1039/C6CS00296J.
Kawai, K.; Ieda, N.; Aizawa, K.; Suzuki, T.; Miyata, N.; Nakagawa, H. A Reductant-Resistant and Metal-Free Fluorescent Probe for Nitroxyl Applicable to Living Cells. J. Am. Chem. Soc. 2013, 135 (34), 12690-12696. https://doi.org/10.1021/ja404757s.
Kierat, R. M.; Kramer, R. A Fluorogenic and Chromogenic Probe That Detects the Esterase Activity of Trace Copper (II). Bioorg. Med. Chem. Lett. 2005, 15 (21), 4824-4827. https://doi.org/10.1016/j.bmcl.2005.07.042.
Knox, H. J.; Chan, J. Acoustogenic Probes: A New Frontier in Photoacoustic Imaging. Acc. Chem. Res. 2018, 51 (11), 2897-2905. https://doi.org/10.1021/acs.accounts.8b00351.
Kojima, R.; Takakura, H.; Kamiya, M.; Kobayashi, E.; Komatsu, T.; Ueno, T.; Terai, T.; Hanaoka, K.; Nagano, T.; Urano, Y. Development of a Sensitive Bioluminogenic Probe for Imaging Highly Reactive Oxygen Species in Living Rats. Angew. Chemie Int. Ed. 2015, 54 (49), 14768-14771. https://doi.org/10.1002/anie.201507530.
Kozminski, P.; Halik, P. K.; Chesori, R.; Gniazdowska, E. Overview of Dual-Acting Drug Methotrexate in Different Neurological Diseases, Autoimmune Pathologies and Cancers. Int. J. Mol. Sci. 2020, 21 (10), 3483. https://doi.org/10.3390/ijms21103483.
Kuchimaru, T.; Iwano, S.; Kiyama, M.; Mitsumata, S.; Kadonosono, T.; Niwa, H.; Maki, S.; Kizaka-Kondoh, S. A Luciferin Analogue Generating Near-Infrared Bioluminescence Achieves Highly Sensitive Deep-Tissue Imaging. Nat. Commun. 2016, 7 (1), 11856. https://doi.org/10.1038/ncomms11856.
Lavis, L. D. Ester Bonds in Prodrugs. ACS Chem. Biol. 2008, 3 (4), 203-206. https://doi.org/10.1021/cb800065s.
Li, H.; Zhang, P.; Smaga, L. P.; Hoffman, R. A.; Chan, J. Photoacoustic Probes for Ratiometric Imaging of Copper(II). J. Am. Chem. Soc. 2015, 137 (50), 15628-15631. https://doi.org/10.1021/jacs.5b10504.
Li, J.-B.; Chen, L.; Wang, Q.; Liu, H.-W.; Hu, X.-X.; Yuan, L.; Zhang, X.-B. A Bioluminescent Probe for Imaging Endogenous Peroxynitrite in Living Cells and Mice. Anal. Chem. 2018, 90 (6), 4167-4173. https://doi.org/10.1021/acs.analchem.8b00198.
Li, J.; Chen, L.; Du, L.; Li, M. Cage the Firefly Luciferin!—A Strategy for Developing Bioluminescent Probes. Chem. Soc. Rev. 2013, 42 (2), 662-676. https://doi.org/10.1039/C2CS35249D.
Lie Ken Jie, M. S. F.; Leung, D. W. Y. Preparation of 1-Phenyl Alkyl Esters of Medium and Long-Chain Fatty Acids. Chem. Phys. Lipids 1989, 50 (2), 155-161. https://doi.org/10.1016/0009-3084(89)90039-X.
Lipinski, C. A.; Lombardo, F.; Dominy, B. W.; Feeney, P. J. Experimental and Computational Approaches to Estimate Solubility and Permeability in Drug Discovery and Development Settings1PII of Original Article: S0169-409X(96)00423-1. The Article Was Originally Published in Advanced Drug Delivery Reviews 23 (1997) 3. Adv. Drug Deliv. Rev. 2001, 46 (1), 3-26. https://doi.org/https://doi.org/10.1016/S0169-409X(00)00129-0.
Liu, C.; Chen, W.; Shi, W.; Peng, B.; Zhao, Y.; Ma, H.; Xian, M. Rational Design and Bioimaging Applications of Highly Selective Fluorescence Probes for Hydrogen Polysulfides. J. Am.Chem. Soc. 2014, 136 (20), 7257-7260. https://doi.org/10.1021/ja502968x.
Liu, C.; Pan, J.; Li, S.; Zhao, Y.; Wu, L. Y.; Berkman, C. E.; Whorton, A. R.; Xian, M. Capture and Visualization of Hydrogen Sulfide by a Fluorescent Probe. Angew. Chemie Int. Ed. 2011, 50 10327-10329. https://doi.org/10.1002/anie.201104305.
Liu, C.; Peng, B.; Li, S.; Park, C.-M.; Whorton, A. R.; Xian, M. Reaction Based Fluorescent Probes for Hydrogen Sulfide. Org. Lett. 2012, 14 (8), 2184-2187. https://doi.org/10.1021/ol3008183.
Martin, R. B. Acid-Catalyzed Ester Hydrolysis. J. Am. Chem. Soc. 1967, 89 (10), 2501-2502. https://doi.org/10.1021/ja00986a057.
Meisenheimer, P. L.; Uyeda, H. T.; Ma, D.; Sobol, M.; McDougall, M. G.; Corona, C.; Simpson, D.; Klaubert, D. H.; Cali, J. J. Proluciferin Acetals as Bioluminogenic Substrates for Cytochrome P450 Activity and Probes for CYP3A Inhibition. Drug Metab. Dispos. 2011, 39 (12), 2403-2410. https://doi.org/10.1124/dmd.111.041541.
Minta, A.; Kao, J. P. Y.; Tsien, R. Y. Fluorescent Indicators for Cytosolic Calcium Based on Rhodamine and Fluorescein Chromophores. J. Biol. Chem. 1989, 264 (14), 8171-8178. https://doi.org/10.1016/S0021-9258(18)83165-9.
Miska, W.; Geiger, R. Synthesis and Characterization of Luciferin Derivatives for Use in Bioluminescence Enhanced Enzyme Immunoassays. New Ultrasensitive Detection Systems for Enzyme Immunoassays, I. Clin. Chem. Lab. Med. 1987, 25 (1). https://doi.org/10.1515/cclm.1987.25.1.23.
Mix, K. A.; Lomax, J. E.; Raines, R. T. Cytosolic Delivery of Proteins by Bioreversible Esterification. J. Am. Chem. Soc. 2017, 139 (41), 14396-14398. https://doi.org/10.1021/jacs.7b06597.
Mofford, D. M.; Adams, S. T.; Reddy, G. S. K. K.; Reddy, G. R.; Miller, S. C. Luciferin Amides Enable in Vivo Bioluminescence Detection of Endogenous Fatty Acid Amide Hydrolase Activity. J. Am. Chem. Soc. 2015, 137 (27), 8684-8687. https://doi.org/10.1021/jacs.5b04357.
Monsees, T.; Miska, W.; Geiger, R. Synthesis and Characterization of a Bioluminogenic Substrate for α-Chymotrypsin. Anal. Biochem. 1994, 221 (2), 329-334. https://doi.org/10.1006/abio.1994.1421.

1 2 3 4

BL660 (R = H)
BL660-Me (R = Me)
4 (R = Ph$^i$Pr)

MTX (R = H)
MTX-$Me_2$ (R = Me)
MTX-$(Ph^iPr)_2$ (R = Ph$^i$Pr)

| Conc. (μM) | MTX-$Me_2$ | MTX-$(Ph^iPr)_2$ |
|---|---|---|
| 0.001 | 1.11 ± 0.06 | 1.04 ± 0.10 |
| 0.01 | 1.05 ± 0.05 | 0.96 ± 0.01 |
| 0.1 | 1.09 ± 0.11 | 1.03 ± 0.06 |
| 1 | 0.77 ± 0.03 | 1.01 ± 0.02 |
| 10 | 0.63 ± 0.08 | 1.04 ± 0.06 |

| Time (min) | Mouse 1 | Mouse 2 | Mouse 3 | Ave | Stdev |
|---|---|---|---|---|---|
| 0 | 2546 | 2250 | 2181 | 2325.7 | 193.9 |
| 5 | 17720 | 12398 | 10929 | 13682.3 | 3573.0 |
| 15 | 19393 | 14989 | 15278 | 16553.3 | 2463.5 |
| 30 | 17941 | 10975 | 7835 | 12250.3 | 5172.3 |
| 45 | 18332 | 10873 | 7648 | 12284.3 | 5480.0 |
| 60 | 14464 | 10761 | 10325 | 11850.0 | 2274.3 |
| 75 | 14089 | 8921 | 8994 | 10668.0 | 2962.9 |
FIG. 17
| Time (min) | Mouse 1 | Mouse 2 | Mouse 3 | Ave | Stdev |
|---|---|---|---|---|---|
| 0 | 2307 | 2458 | 2025 | 2263.3 | 219.8 |
| 5 | 2427 | 3409 | 2563 | 2799.7 | 532.1 |
| 15 | 4763 | 3680 | 3443 | 3962.0 | 703.7 |
| 30 | 3664 | 3162 | 2677 | 3167.7 | 493.5 |
| 45 | 3586 | 3030 | 2724 | 3113.3 | 437.0 |
| 60 | 3678 | 2866 | 2157 | 2900.3 | 761.1 |
| 75 | 3120 | 2559 | 2300 | 2659.7 | 419.2 |
FIG. 18
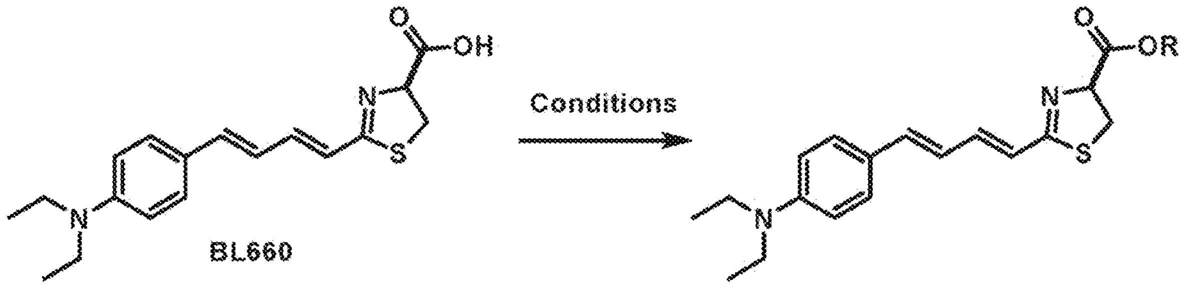
1 2 3 4
FIG. 19

HYDROLYSIS-RESISTANT ESTERS FOR DRUG AND IMAGING AGENT DELIVERY

CROSS-REFERENCE TO RELATED APPLICATIONS

This patent application claims benefit of U.S. Patent Application Ser. No. 63/420,787, filed Oct. 31, 2022, which is incorporated herein by reference in its entirety.

STATEMENT REGARDING FEDERALLY SPONSORED RESEARCH OR DEVELOPMENT

This invention was made with government support under 1R35GM133581-01 awarded by the National Institutes of Health. The United States Government has certain rights in the invention.

FIELD OF THE INVENTION

The present disclosure relates to the bioavailability and cell permeability of substrate molecules of small-molecule drugs, imaging agents, or activity-based sensing (ABS) probes, and more particularly, to carboxylate substrates converted to benzyl ester to enhance admission into mammalian cell walls.

BACKGROUND

ABS probes equipped with a NIR BL readout are promising chemical tools to study cancer biomarkers owing to their high sensitivity and deep tissue compatibility. However, the standard approach of installing a responsive trigger at the aniline site through a self-immolative linker is not suitable for NIR substrates because they require N,N-dialkylation at this position to achieve NIR emission. Capping the carboxylate is also unfavorable due to the instability of the resulting ester moiety which would result in high background signals.

The bioavailability and cell permeability of small-molecule drugs, imaging agents, or ABS probes are largely dictated by molecular weight, lipophilicity, hydrogen bonding ability and net charge. For instance, a positively charged or neutral molecule is more likely to gain entry into a cell compared to an anion owing to Coulombic repulsion caused by the negatively charged cell membrane. A reliable strategy to improve cell uptake is to temporarily mask the negative functional group. For example, carboxylates can be readily transformed into the corresponding ester moiety, which upon crossing the cell membrane, can be cleaved to unmask the latent charge via intracellular esterase activity. A notable example is the use of this strategy to facilitate uptake of fluorescent indicators for calcium, which are equipped with a tri- or tetra-carboxylate binding motif. Under normal circumstances, it would be nearly impossible for a molecule with a net charge of −3 or −4 to enter the cell. However, calcium indicators for cellular imaging are routinely prepared and sold in the acetoxy methyl ester form. Beyond the modification of small molecules, this approach has extended to facilitate the delivery of functional proteins through the conversion of surface-exposed carboxylates to esters, as has been done, for example, for the delivery of GFP (green fluorescent protein) and human ribonuclease. However, there are limitations that must be considered when carboxylate-masking is employed in vivo for the purpose of targeted cargo delivery. First, most esters are prone to spontaneous hydrolysis under acidic, neutral, or basic conditions, while the body features numerous pH gradients (e.g., the pH in the gastrointestinal tract ranges from 5.7 to 7.4), which will result in off-target delivery upon systemic administration. Second, ester-hydrolyzing enzymes are ubiquitously expressed throughout the body in nearly all cell types, leading to indiscriminate cargo release. In general, ester stability is correlated to size and this property has been leveraged to tune the pharmacokinetics of drugs such as androgens. In the context of ABS, an assortment of ester-based probes exists; however, an important distinction is that the carboxylate is a component of the trigger and not of the reporter.

Amongst the ABS probes designed for in vivo applications, those equipped with a BL readout are highly coveted. Unlike fluorescence-based probes which require external light excitation to generate a signal, BL results from luciferase-mediated light production and thus, is highly sensitive due to low background. Moreover, the structure of luciferase substrates can be modified to shift the emission wavelength into the NIR to achieve greater tissue penetration. Regardless of the variant, a viable substrate must contain a free carboxylate group for enzyme recognition and subsequent light generation. Unfortunately, the presence of a negative charge adversely impacts cell permeability. To yield an appreciable BL signal in vivo, luciferin must be administered systemically at exorbitant levels (>150 mg/kg). Recently, we reported the development of BL660-NO (a nitric oxide (NO)-responsive probe) by amidating the carboxylate of BL660 (a NIR BL substrate) with O-phenylene diamine. We found that this modification dramatically improved cell permeability (in vivo dosing decreased to 1 mg/kg), prompting us to explore the installation of other triggers at this position. Triggers based on para-substituted benzyl alcohol, are the most ubiquitous self-immolative linkers used in modern probe design. Typically, an electron-deficient analyte-responsive trigger occupies the para-position, and the immolative linker is connected to a reporter through a stable ether, carbamate, or carbonate bond. Without wishing to be bound by any particular theory, upon interaction with the target analyte, the trigger is activated to yield a more electron-rich moiety. Flow of electron density into the aromatic ring facilitates formation of a quinone methide (or aza-quinone methide) intermediate which is coupled to the spontaneous release of the latent reporter. We hypothesized inclusion of additional phenyl or alkyl groups at the benzyl position can impart stability by shielding the ester from water or other nucleophiles. Further, we envisioned installing these onto BL660 would enable monitoring of stability using BL imaging. However, upon surveying the literature, we discovered the available options were limited to hydrolytically stable groups (e.g., amides, aldehydes, etc.), with a few examples of simple esters. As represented in FIG. 6*a* herein, however, prior art ester ABS probes suffer from instability in vivo.

SUMMARY

In one exemplary embodiment according the present disclosure, the invention provides a compound of the formula:

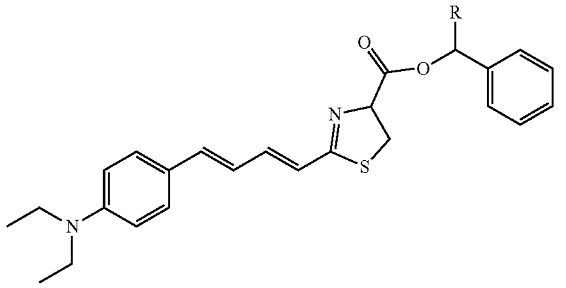

and R may be selected from the group consisting of methyl, phenyl, isopropyl, isobutyl and isopentyl.

In a more specific embodiment, the stabilizing substitution on the benzylic position may comprise a phenyl group. Alternatively, a stabilizing substitution on the benzylic position may be an isopropyl group.

According to another aspect, the phenyl group adjacent to R may have a NO2 functional group nitroreductase or hypoxia ni trigger.

In another embodiments, the invention relates to methotrexate modified to have a benzyl ester group as described herein. In one particular embodiment the invention provides a methotrexate of the formula:

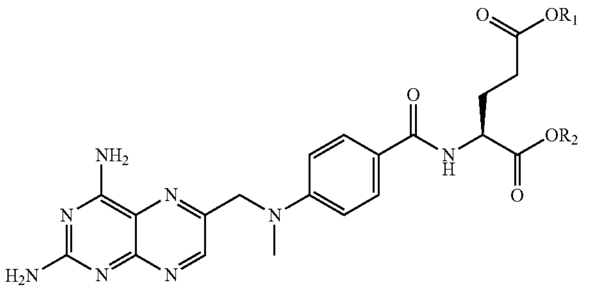

wherein

R1 may be —H or a substituted benzyl ester group comprising a stabilizing substitution on the benzylic position, wherein the stabilizing substitution on the benzylic position comprises phenyl or a branched $C_3$-$C_5$ alkyl group, and R2 may be —H or a substituted benzyl ester group comprising a stabilizing substitution on the benzylic position, wherein the stabilizing substitution on the benzylic position comprises phenyl or a branched $C_3$-$C_5$ alkyl group, provided that R1 and R2 are not both —H.

In another aspect, this invention provides method of imaging mammalian cells, comprising: inoculating the mammal with a carboxylic luciferin substrate compound of the formula:

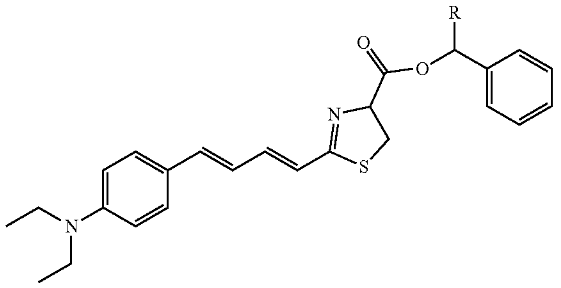

wherein R is selected from the group consisting of —H, methyl, phenyl, isopropyl, isobutyl and isopentyl. In one embodiment, R comprises a phenyl group. In another embodiment, R comprises an isopropyl group. Optionally, the phenyl group has a trigger, for example, a nitro group —$NO_2$ in the para or meta position.

According to still another aspect, this invention provides an improvement in the administration of methoxtrate for treatment of cancer, the improvement comprising administration of A methotrexate compound of the formula:

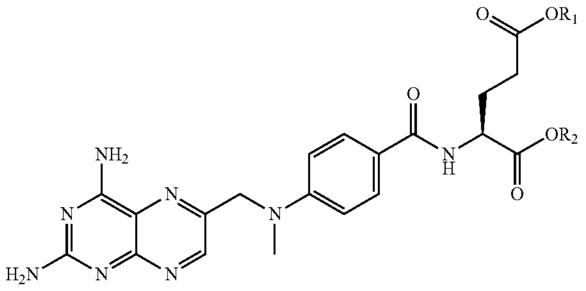

wherein R1 and R2 may be the same or different and either may be a substituted benzyl ester group comprising a stabilizing substitution on the benzylic position, wherein the stabilizing substitution on the benzylic position comprises phenyl or a branched $C_3$-$C_5$ alkyl group, provided that R1 and R2 are not both —H. Optionally, the phenyl group in R1 and/or R2 may have a trigger group in the para or meta position.

Further embodiments, forms, features, aspects, benefits, objects, and advantages of the present application shall become apparent from the detailed description and figures provided herewith.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A more complete appreciation of the present disclosure and many of the attendant advantages thereof will be readily obtained as the same becomes better understood by reference to the following detailed description when considered in connection with the accompanying drawings, wherein:

FIG. 17 is a table of total luminescence count for each mouse treated with BL660-NTR systemically via retroorbital injection. Values obtained by summing ROIs drawn around each tumor for each animal. Time point=0 min represents background scans before dye administration;

FIG. 18 is a table of total luminescence count for each mouse treated with Compound 4 systemically via retroorbital injection. Values obtained by summing ROIs drawn around each tumor for each animal. Time point=0 min represents background scans before dye administration;

FIG. 19 shows synthesis routes for Compounds (1), (2), (3), and (4) according to various embodiments, wherein the indicated "Conditions" are described herein.

DETAILED DESCRIPTION

Figure 1A:
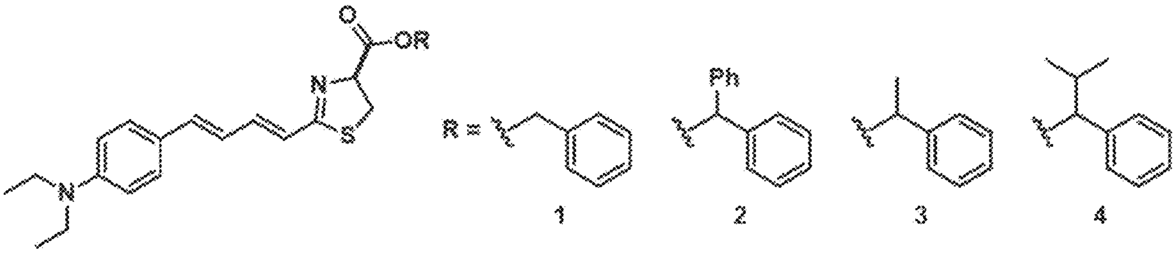
FIG. 1A shows chemical structures of four BL660 ester compounds in accordance with various embodiments of the invention, wherein various benzyl R groups are labeled 1-4 respectively, and the resulting compounds are referred to herein as Compound (1), Compound (2), Compound (3), and Compound (4), respectively or, where context permits, simply (1), (2), (3) and (4)

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

In a general aspect, this invention provides a method for masking carboxyl groups on two chemical substrate molecules having utility in mammalian cells, to facilitate passage of the molecules through cell membranes. In one aspect, the substrate may be a luciferin-type imaging agent BL660; in another aspect, the substrate may be methotrexate. Both substrates have in vivo applications for mammalian cells as an imaging agent or activity-based sensing (ABS) probe, or for treatment of cancer, respectively. Each of the substrates has at least one carboxyl group.

In accordance with another aspect of this invention, the at least one carboxyl group is masked by a benzyl ester group. According to another, optional aspect, the benzyl ester group may carry a stabilizing substitution on the benzylic position.

The benzyl ester group may sometimes be referred to herein as a 'linker' or a 'prodrug linker.'

Without wishing to be bound by any particular theory, the benzyl ester groups described herein are believed to reduce the resistance to entry into the cell by masking the carboxyl groups and imbuing the substrate with a more neutral charge. The masking group may be structurally designed so that the resulting ester is resistant to hydrolysis in vivo by lysing enzymes such as luciferase and/or others ordinarily present. Nevertheless, the masking group in some embodiments needs to be liable to separation from the molecule inside the cell in order to activate the substrate molecule to function as an imaging agent or anticancer drug, accordingly.

In one aspect, the benzylic position substitution may be a phenyl group or a branched alkyl group, exemplified herein in FIG. la as Compounds (3), (2) and (4), respectively, to impart resistance to hydrolysis. Illustrative branched alkyl groups for this invention include isopropyl, isobutyl and isopentyl (i.e., $C_3$-$C_5$).

Optionally, there is a trigger group at the para position or ortho position or both on the phenyl ring of the benzyl ester group. The trigger group is selected to be responsive to a desired target in a cell, such that reaction with the target causes a self-immolative reaction which releases the benzyl ester group from the substrate to unmask the carboxyl group and thus enable the substrate to exhibit its activity more quickly in the presence of the target than elsewhere. The ester group may be described as a self-immolative linker. Providing the trigger group makes the compound more active in the presence of the target and thus helps make an imaging molecule more useful as a probe, and it may enhance the utility of a drug. The target may be, for example, a chemical structure, or a condition in the cell such as hypoxia. Upon a reading and understanding of the present disclosure by one of skill in the art, numerous trigger and target pairs will be understood to be known and expected to be effective for use in the present invention. For example, Cu(I) could be the target of a tris(2-pyridylmethyl)amine trigger group; hydrogen peroxide could be the trigger for a boronate ester trigger group; hypoxia could be a target for an N-oxide dialkylalinine trigger group, etc.

In some embodiments, the substrate is a molecule that serves as an ABS probe that is useful for NIR BL imaging for the detection of tumor hypoxia. In one specific but illustrative embodiment, a luciferin bioluminescent imaging agent of the formula (S)-2-((1E,3E)-4-(4-(diethylamino)phenyl)buta-1,3-dien-1-yl)-4,5-dihydrothiazole-4-carboxylic acid, designated herein as "BL660," is modified to mask the carboxyl group with a self-immolative ester in accordance with this invention for use as an imaging agent in mammalian cells.

In other embodiments, substrate is a pharmaceutically active molecule e.g., methotrexate.

The utility of the ester in providing carboxylate masking to allow the substrate molecules to pass through a cell wall, resist hydrolysis and remain active for the intended effect is demonstrated herein.

Design and Synthesis of Substituted Benzyl Esters

One aspect of this invention provides ABS probes for the BL modality via carboxylate-masking. Triggers based on para-substituted benzyl alcohol, are the most ubiquitous self-immolative linkers used in modern probe design. Typically, an electron-deficient analyte-responsive trigger occupies the para-position, and the immolative linker is connected to a reporter through a stable ether, carbamate, or carbonate bond. Upon interaction with the target analyte, the trigger is activated to yield a more electron-rich moiety. Flow of electron density into the aromatic ring facilitates formation of a quinone methide (or aza-quinone methide) intermediate which is coupled to the spontaneous release of the latent reporter. In accordance with various embodiments, phenyl or alkyl groups are included at the benzyl position and are shown to provide stability as observed using BL (bioluminescent) imaging.

The esters employed in accordance with this invention are depicted in FIG. 1*a*, wherein include R1=(Ph,H) as a comparative example, R2=($Ph_2$), R3=(PhMe), and R4=a representative branched alkyl group, isopropyl (Ph,$^i$Pr). The resulting esterified compositions are referred to herein as Compound (1), Compound (2), Compound (3) and Compound (4) respectively or, where context permits, simply (1), (2), (3) or (4). Compound (4) is also referred to as BL660-NTR.

The synthesis of Compound (1), Compound (2), and Compound (3) from BL660 was routine. In general, the carboxylic acid was converted to an acyl fluoride which was then reacted with appropriate benzyl alcohol starting materials.

The esterification of BL660 to afford Compound (4) proved to be challenging owing to the bulky nature of this benzyl alcohol relative to Compound (2). Conventional reaction conditions to form esters including Fischer, Mitsunobu, Steglich and Yamaguchi esterification failed to give products in appreciable yields beyond trace conversion. Moreover, we observed racemization of the chiral center housing the carboxylate. This is detrimental because stereochemistry at this position is required for luciferase recognition. Similarly, activation to the acyl chloride, followed by addition of the benzyl alcohol gave complex, inseparable mixtures. Our efforts to control the rate of alcohol addition, molarity of the reaction, stoichiometry of the components, and temperature were all unsuccessful. We also found that diazo chemistry was incompatible with our system. Ultimately, we employed cyanuric fluoride at −20° C. to access the less reactive acyl fluoride intermediate, which upon reaction with the corresponding benzyl alcohol yields the desired esters. Of note, no attempts were made to separate the stereoisomers for Compound (3) and Compound (4). All subsequent analyses were performed on the mixtures and reported as 'apparent' results.

Assessment of Hydrolytic Stability and Esterase Reactivity

Figure 8:
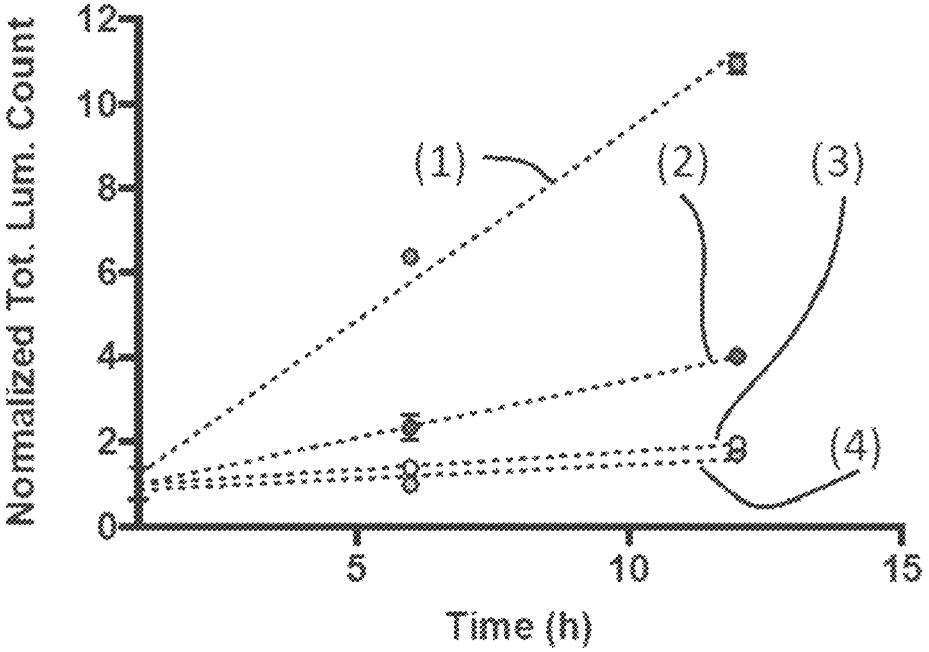
FIG. 8 is a graph of normalized total luminescence count of Compounds (1), (2), (3), and (4) of FIG. 1A incubated in PBS (pH 7.4) at 37° C. for 1, 6, and 12 hours. n=3 for each timepoint.
Figure 9A:
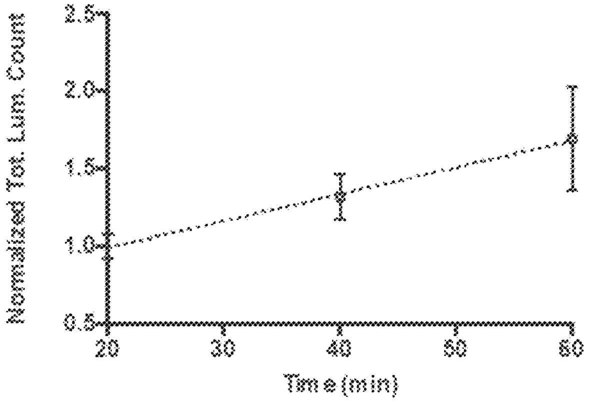
FIG. 9A is a graph of normalized total luminescence count of Compound (1) after treatment with porcine liver esterase (0.1 units/mL) at 37° C. for 10 20, 30, 45, and 60 mins. n=3 for each timepoint.
Figure 9B:
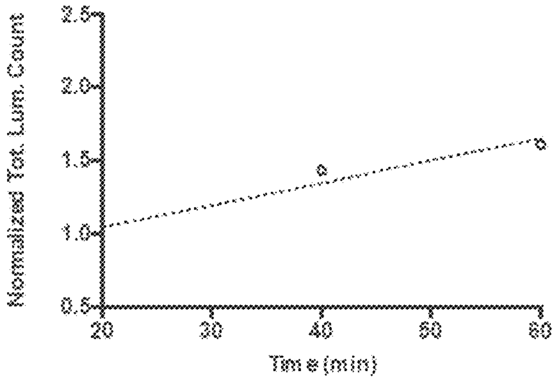
FIG. 9B is a graph of normalized total luminescence count of Compound (2) after treatment with porcine liver esterase (0.1 units/mL) at 37° C. for 10 20, 30, 45, and 60 mins. n=3 for each timepoint.
Figure 9C:
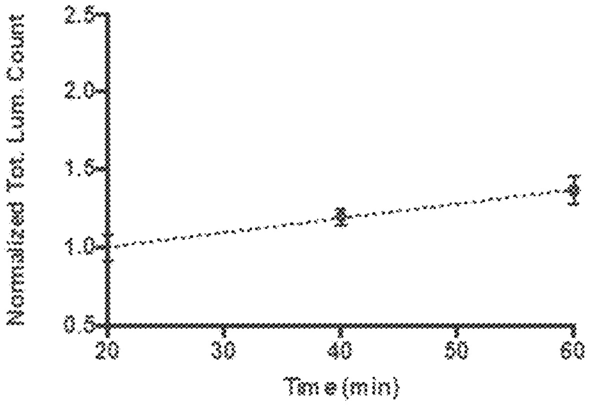
FIG. 9C is a graph of normalized total luminescence count of Compound (3) after treatment with porcine liver esterase (0.1 units/mL) at 37° C. for 10 20, 30, 45, and 60 mins. n=3 for each timepoint.
Figure 9D:
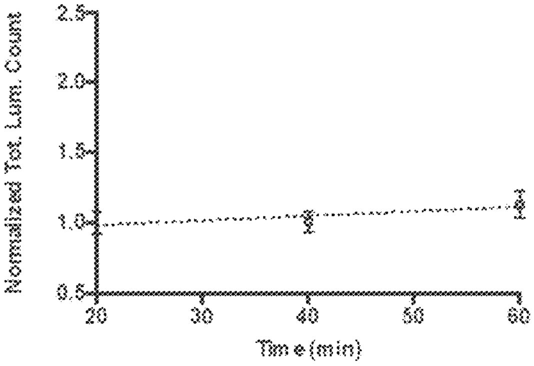
FIG. 9D is a graph of normalized total luminescence count of Compound (4) after treatment with porcine liver esterase (0.1 units/mL) at 37° C. for 10 20, 30, 45, and 60 mins. n=3 for each timepoint.

We began our analysis of stability by incubating BL660 esters of Compound (1), Compound (2), and Compound (3) at 37° C. in PBS (phosphate-buffered saline) (pH 7.4). After 1, 6, and 12 hours, luciferase was added (10mU, 37° C., pH 7.4) to initiate BL production. The rate of hydrolysis, reported as total luminescence counts per hour, indicates hydrolysis in descending order is: Compound (1) ($13.9\pm1.4\times10^3$); Compound (2) ($3.3\pm0.6\times10^3$), and Compound (3) ($1.0\pm0.1\times10^3$) (FIG. 1*b*, wherein the esters are indicated on the horizontal axis) and FIG. 8 (wherein the respective timeline plots are identified beneath the horizontal axis as (1), (2), etc.). Luminescent counts were recorded using an IVIS In Vivo Imaging System. These results show the methyl substituent of (3) is over three-fold more effective at blocking hydrolysis than the phenyl group of (2). Without wishing to be bound by any theory, we speculate hydrolysis of (3) may involve an $S_N1$ mechanism, thus favoring formation of a double benzylic carbocation.

Figure 1B:
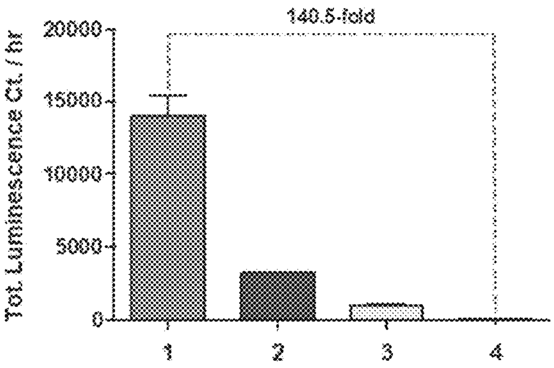
FIG. 1B is a bar graph comparing total luminescence count per hour for Compounds (1), (2), (3), and (4) of FIG. 1A (10 μM) incubated in PBS (pH 7.4) at 37° C. for 1, 6, and 12 hrs. (n=3)
Figure 1C:
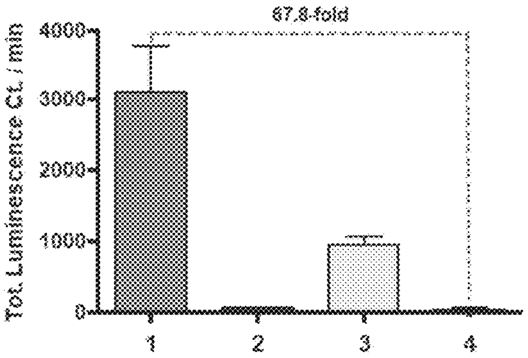
FIG. 1C is a bar graph comparing total luminescence count per minute for Compounds (1), (2), (3), and (4) (10 μM) after treatment with porcine liver esterase (0.1 units/mL) at 37° C. for 20, 40, and 60 mins. (n=3)

When the same panel was treated with porcine liver esterase (0.1 units/mL, 37° C., pH 7.4) for 20, 40, and 60 minutes, we found that Compound (2) was most resistant toward enzymatic degradation. The enzymatic rates, reported as total luminescence counts per minute, in descending order are: Compound (1) ($31.0\pm6.8\times10^2$), (3) ($9.5\pm1.2\times10^2$), and (2) ($0.6\pm0.1\times10^2$) (FIG. 1*c* and FIG. 9). The greater stability imparted by the aromatic ring is not surprising since esterase reactivity can be readily attenuated with bulkier substituents. With this data, we hypothesized, without wishing to be bound by any theory, the hydrolytic stability of (3) can be retained (or improved) by switching to a larger alkyl group with multiple rotatable bonds (i.e., isopropyl ($^i$Pr)), while simultaneously suppressing esterase reactivity. Relative to the parent benzyl ester, Compound (4) is about 140-fold more resistant to hydrolysis and exhibits about 68-fold greater esterase stability (FIG. 1*b* and FIG. 1*c*).

Figure 1D:
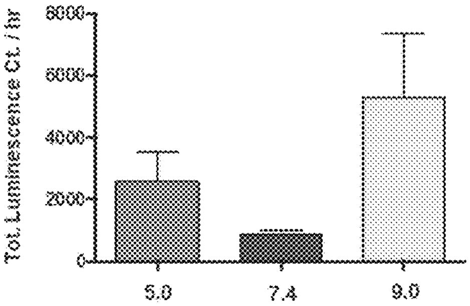
FIG. 1D is bar graph comparing total luminescence count per hour for Compound (4) at (10 μM) at pH 5.0, 7.4, and 9.0 at 37° C. for 2, 3, and 4 hrs. (n=3)
Figure 1E:
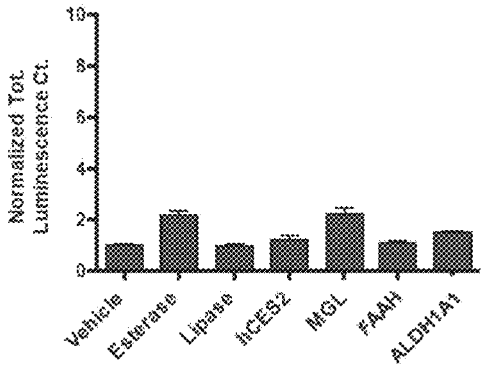
FIG. 1E is a bar graph showing normalized total luminescence count for Compound (4) (5 μM) exposed to various ester-hydrolyzing enzymes. (n=3)

Following this set of experiments, we subjected Compound (4) to acidic (pH 5) and alkaline (pH 9) conditions to account for the various pH gradients in the body. For these experiments we used the Britton-Robinson buffer system. As reported in total luminescence counts per hour, (4) was most stable at pH 7.4 ($8.6\pm1.3\times10^2$), followed by pH 5.0 ($25.7\pm9.6\times10^2$), and finally pH 9.0 ($52.8\pm20.7\times10^2$) (FIG. 1*d*). Lastly, we examined the stability of (4) against a panel of enzymes beyond porcine liver esterase that are known to possess ester-cleaving activity. These include lipase, human carboxyesterase-2, monoacylglycerol lipase, fatty acid amide hydrolase, and aldehyde dehydrogenase 1A1. Remarkably, exposure to high levels of these enzymes over a period of one hour resulted in minimal activation (FIG. 1*e*).

Demonstration of Ph$^i$Pr Ester Stability in Live Cells

Next, two complementary cellular experiments we conducted to determine whether the excellent in vitro performance noted above translates within a more complex cellular environment where many esterase isoforms are present. Moreover, we aimed to determine whether the Ph$^i$Pr ester will have a similar effect on other molecules with diverse chemical structures beyond BL660.

Figure 2A:
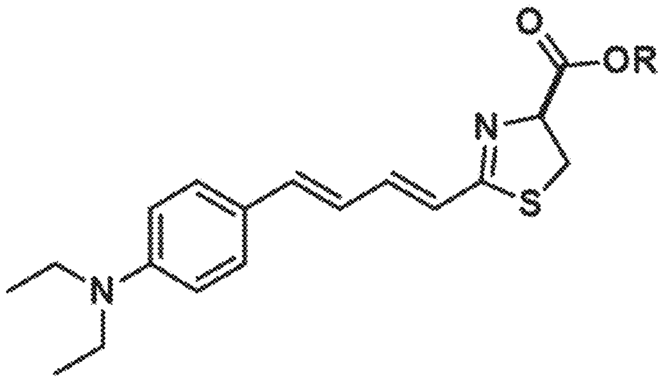
FIG. 2A shows chemical structures of BL660 (R═H), a methyl ester derivative (comparative example), and Compound (4) of FIG. 1A.
Figure 3A:
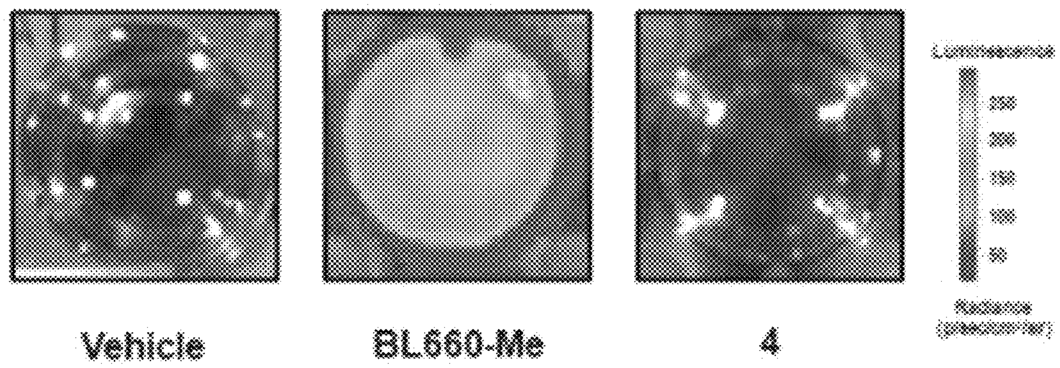
FIG. 3A shows representative COLOR BL images of 4T1-Luc cells plated in 24-well plates treated with DMSO (vehicle); BL660-Me; or Compound (4) for 30 mins at 37° C. Probe concentration=10 μM.
Figure 3B:
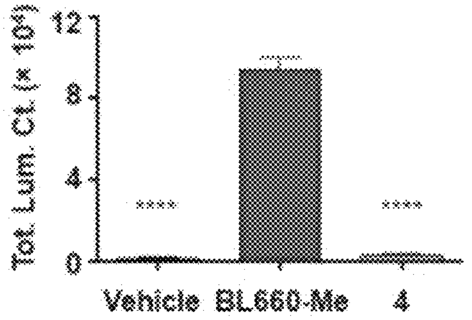
FIG. 3B is a bar graph of total luminescence count per hour$\times10^4$ for plates of FIG. 3A.
Figure 10A:
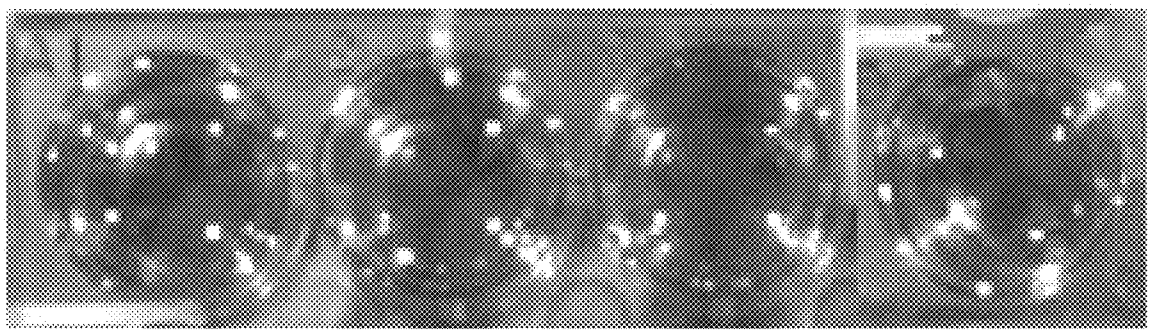
FIG. 10A shows BL images of 4T1-Luc cells plated in 24-well plates treated with DMSO (vehicle) for 30 mins at 37° C. Probe concentration=10 μM. After cropping wells from the same plate, the images were grouped based on the treatment condition.
Figure 10B:
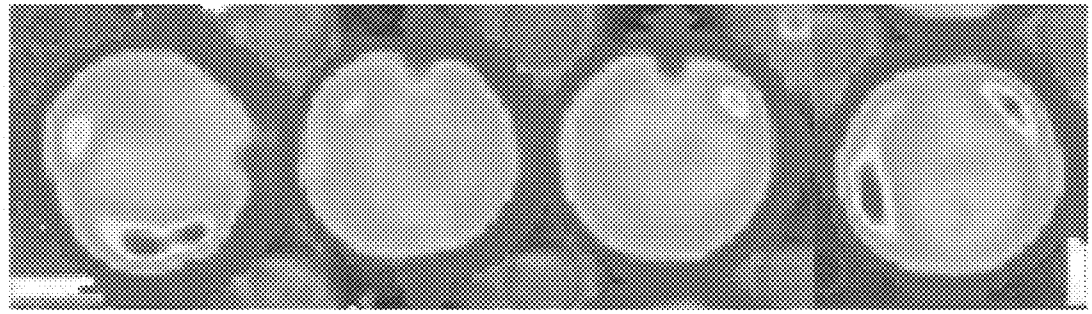
FIG. 10B shows BL images of 4T1-Luc cells plated in 24-well plates treated with BL660-Me for 30 mins at 37° C. Probe concentration=10 μM. After cropping wells from the same plate, the images were grouped based on the treatment condition.
Figure 10C:
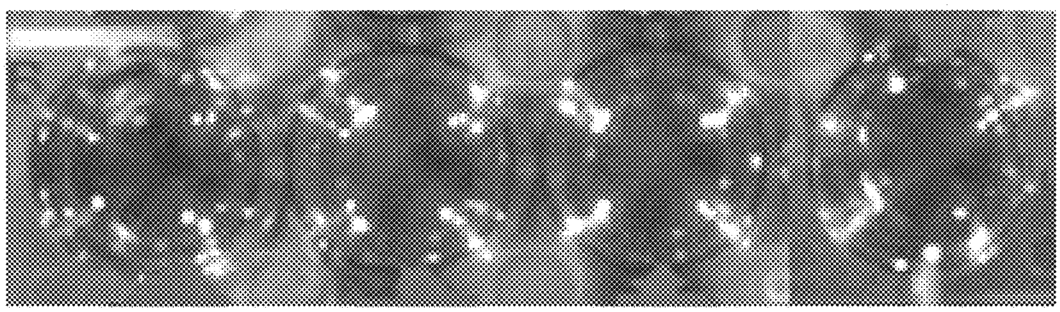
FIG. 10C shows BL images of 4T1-Luc cells plated in 24-well plates treated with Compound (4) for 30 mins at 37° C. Probe concentration=10 μM. After cropping wells from the same plate, the images were grouped based on the treatment condition.
Figure 11A:
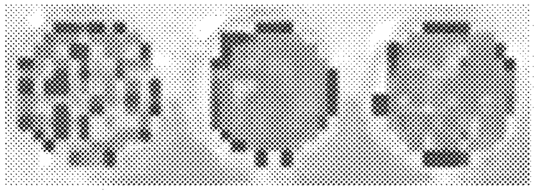
FIG. 11A shows BL images in 96-well plates containing BL660-NTR, NTR, and luciferase according to one embodiment.
Figure 11B:
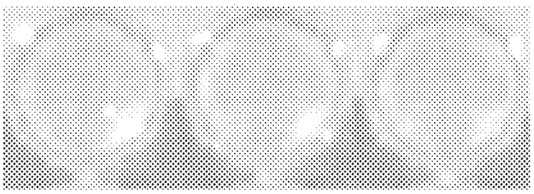
FIG. 11B shows comparative BL images in 96-well plates containing BL660-NTR and luciferase without NTR.
Figure 11C:
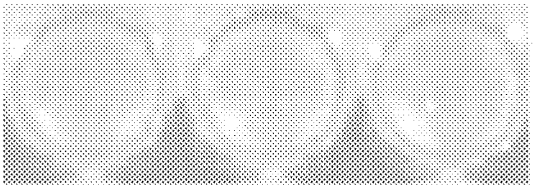
FIG. 11C is shows comparative BL images in 96-well plates containing BL660-NTR and NTR without luciferase.
Figure 11D:
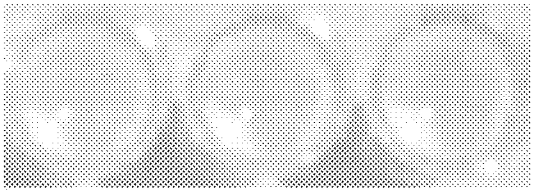
FIG. 11D is shows comparative BL images in 96-well plates containing NTR and luciferase, without BL660-NTR.
Figure 12:
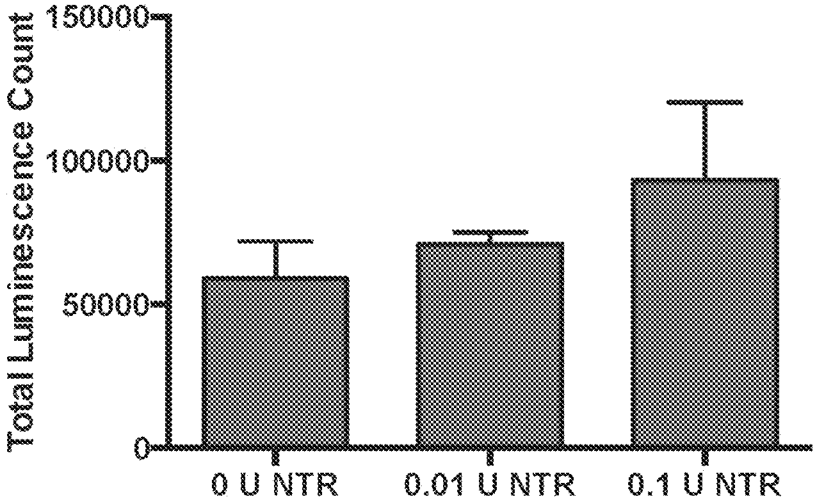
FIG. 12 is a bar graph showing total luminescence count from in vitro assay demonstrating activation of BL660-NTR depends on the concentration of NTR present. n=3 for each condition.

First, we prepared BL660-Me, a methyl ester derivative of BL660 as shown in FIG. 2*a* for comparison to the benzyl ester (4) of FIG. 1*a*. Next, we cultured 4T1 murine breast cancer cells, stably expressing the luciferase enzyme (4T1-Luc). The cells were then treated with a DMSO (dimethyl sulfoxide) vehicle control, BL660-Me or Compound (4) (FIG. 3*a* and FIG. 10*a, b, c* respectively?). Imaging was performed using the IVIS In Vivo Imaging System. Analysis of the imaging results revealed that the total luminescence count for BL660-Me-treated 4T1 cells ($94.1\pm5.9\times10^3$) were 55-fold and 31-fold more luminescent relative to the vehicle ($1.7\pm0.8\times10^3$) and Compound (4) ($3.1\pm1.2\times10^3$) counterparts, respectively (FIG. 3*b*). These results indicate the Ph'Pr ester is stable to the collection of intracellular esterases present in 4T1 cells.

Methotrexate

Figure 2B:
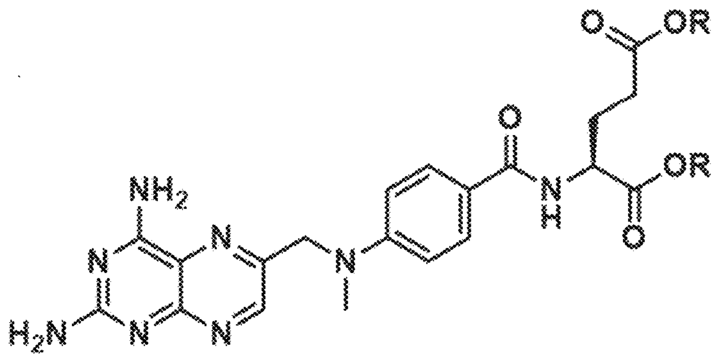
FIG. 2B shows the chemical structure of MTX, a Me derivative (comparative example), and a benzyl ester based on the R4 ($Ph^iPr$) group shown in FIG. 1A.
Figure 3C:
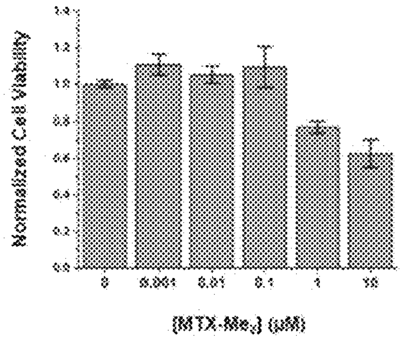
FIG. 3C is a bar graph of normalized MTT cell viability assays for A549 cells treated with MTX-Me at various concentrations for 24 hours. n=3. Error bars=SEM.
Figure 3D:
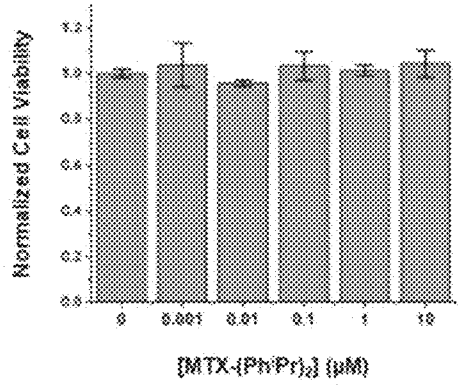
FIG. 3D is a bar graph of normalized MTT cell viability assays for A549 cells treated with MTX-$(Ph^iPr)_2$ at various concentrations for 24 hours. n=3. Error bars=SEM.

Next, we modified the two carboxylates in methotrexate (a potent anticancer and immunosuppressive drug) to afford the methyl (MTX-$Me_2$) or Ph$^i$Pr (MTX-$(Ph^iPr)_2$) ester variants (FIG. 2*b*). A549 cells were cultured and treated with MTX-$Me_2$ or MTX-$(Ph^iPr)_2$ at various concentrations for 24 hours before they were subjected to MTT analyses. Our results revealed the viability was ~63% and 100% at the highest concentration (10 μM) of MTX-$Me_2$ and MTX-$(Ph^iPr)_2$ tested, respectively (FIGS. 3*c* and 3*d*). This experiment demonstrates that the hydrolysis of the esters on MTX-$(Ph^iPr)_2$ is sufficiently slow that the buildup of MTX was inconsequential to the health of the cells. Statistical analysis for FIG. 3*b*, FIG. 3*c* and FIG. 3*d* was performed using a two-tailed t-test ($\alpha$=0.05, **** P<0.001)

Conversion of Ph$^i$Pr Ester Into a Versatile Self-Immolative Linker

Figure 7:
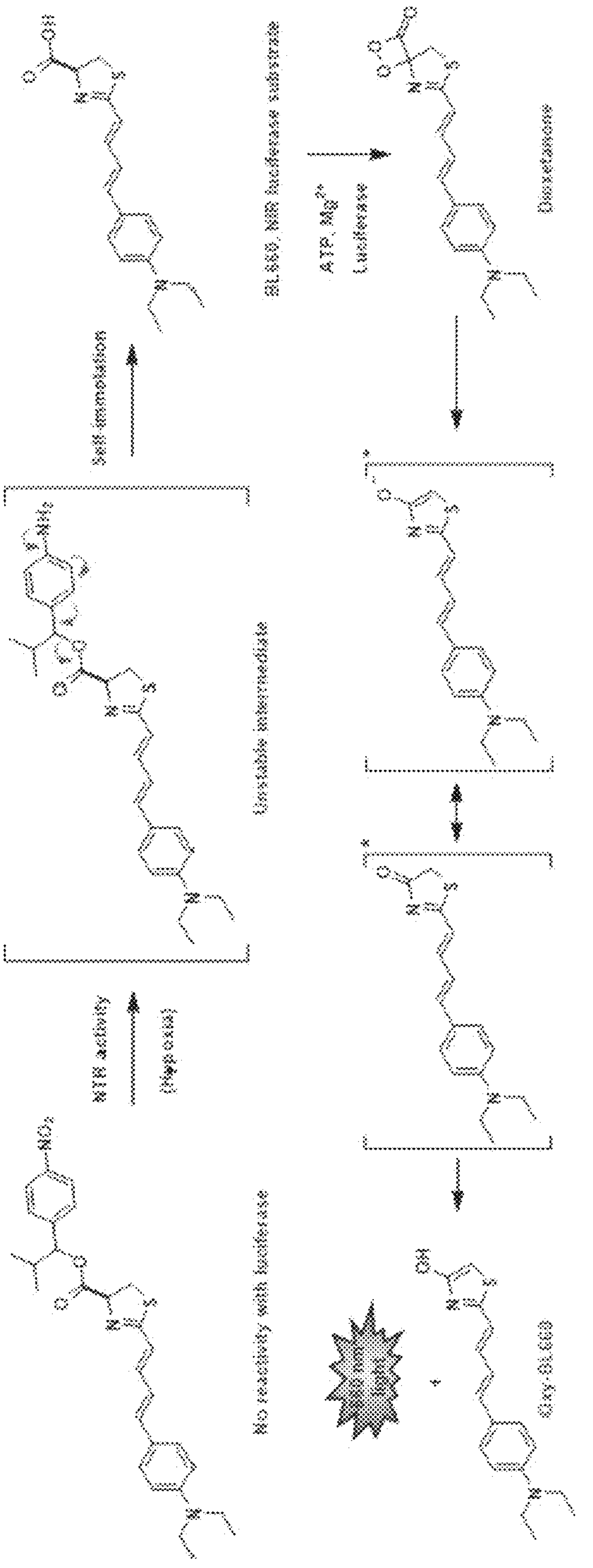
FIG. 7 is a schematic according to another embodiment, showing NTR-mediated activation of BL660-NTR under hypoxic conditions to afford BL660 by contact with nitroreductase, wherein subsequent luciferase-catalyzed conversion to the dioxetanone intermediate is followed by spontaneous decomposition to the oxy-BL660 product to generate NIR BL.

While we envision nearly any electron-deficient trigger can be installed at the para (or ortho) position of the Ph$^i$Pr ester to yield an ABS probe for NIR BL imaging, we strategically selected to use the nitro group to develop BL660-NTR. In addition to its common use in probe design for other modalities, this biomarker is a feature of gram positive and negative bacteria and thus, can be leveraged for sensing bacterial infections. Moreover, NTR can also be employed to detect tumor hypoxia owing to overexpression in many types of solid tumors. Once our probe engages its target in a cell, the aryl nitro moiety can be reduced by nitroreductase, which is normally present in a cell, to afford the electron-rich hydroxylamine or amino products, which initiates self-immolation to release BL660, which emits of a photon at 660 nm. Without wishing to be bound by any particular theory, in the presence of luciferase, this substrate is enzymatically converted to a dioxetanone, which decomposes to generate oxy-BL660 in an excited state, and relaxation to the ground state is accompanied by the emission of a photon at 660 nm. FIG. 7.

Figure 4A:
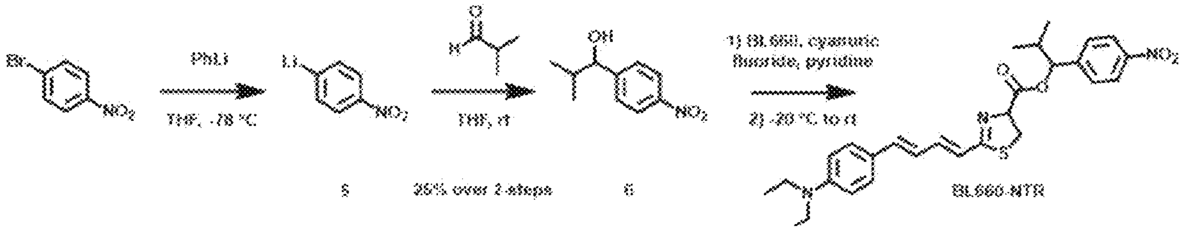
FIG. 4A shows the synthetic route to access BL660-NTR according to one embodiment.

The synthesis of BL660-NTR in the embodiment of FIG. 4*a* began with subjecting 4-nitrobromobenzyme to phenyllithium to initiate a lithium-halogen exchange reaction. The resulting 4-nitrophenyllihtium (Compound 5) intermediate was used directly without purification to attack 2-methyl propanaldehyde to give a 25% yield of benzyl alcohol (6), which carries the —NO2 trigger group in the para position. Then utilizing the acyl fluoride chemistry described above, BL660-NTR was obtained in 10% yield (FIG. 4*a*).

Figure 4B:
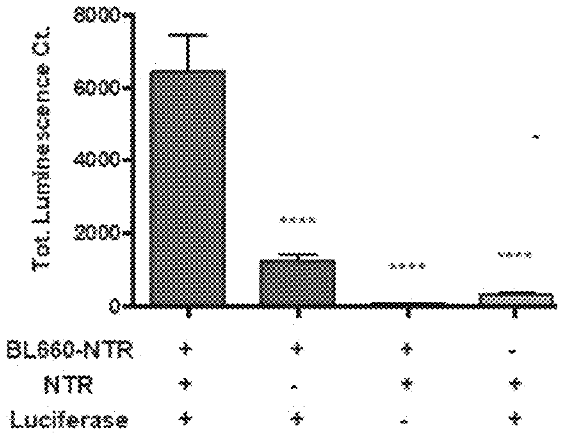
FIG. 4B is a bar graph of total luminescence count from an in vitro assay demonstrating that the probe, NTR, and luciferase must all be present to generate a signal: BL660-NTR (5 μM), NTR (0.1 units), and luciferase (0.0125 mg/mL final concentration)

With BL660-NTR in hand, we performed an in vitro assay to demonstrate that the BL output depends on both NTR and luciferase activity (FIG. 4*b* and FIG. 11). When each component is present, we observed a notable increase in the total luminescence count. However, when NTR (column 2) was absent, the signal was significantly attenuated. Likewise, when luciferase (column 3) or BL660-NTR (column 4) was excluded from the reaction, the signal was minimal and comparable to control wells containing only media and a DMSO vehicle.

Figure 4C:
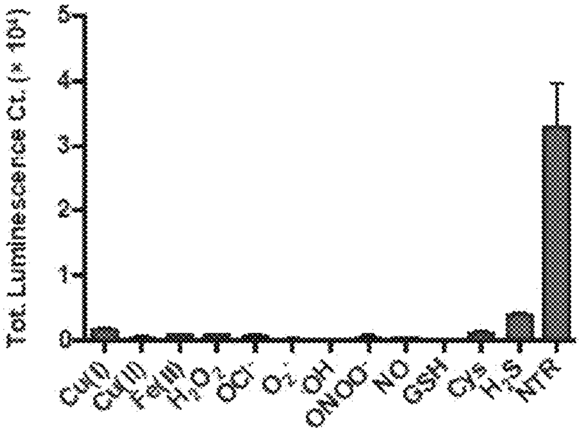
FIG. 4C is a bar graph of total luminescence count response to biologically relevant analytes that may cause interference for BL660-NTR.

Next, we subjected BL660-NTR to various biologically relevant analytes that may contribute to off-target probe activation in vivo. For instance, transition metals like Cu(II) can facilitate ester hydrolysis via Lewis acid-mediated ester activation. Additionally, various reactive oxygen and nitrogen that can interact with the ester bond were also tested. Lastly, we also examined reactive sulfur species, which are known to reduce aryl nitro groups. Under no circumstance did we observe activation greater than 10% compared to the NTR positive control (FIG. 4*c*).

Figure 4D:
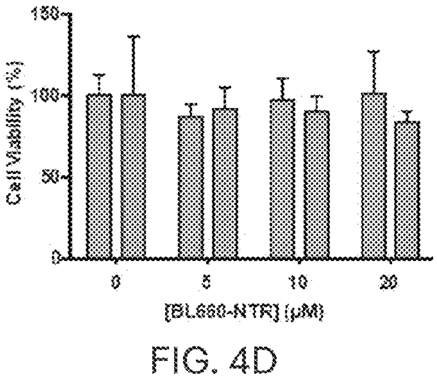
FIG. 4D is a bar graph of MTT assay at various concentrations of BL660-NTR (0, 5, 10, 20 μM), wherein green and orange represents 1- and 3-hour incubation, respectively.

Prior to testing BL660-NTR in vivo, we assessed potential cytotoxicity by treating A549 cells with BL660-NTR across a concentration range of 0 to 20 μM for up to 3 hours. No loss of cell viability was observed (FIG. 4*d*).

Figure 4E:
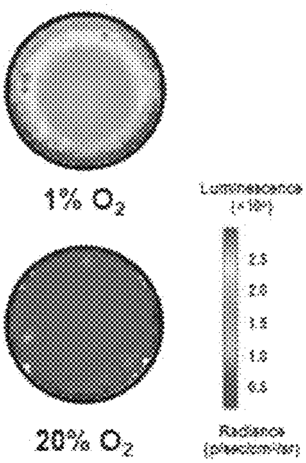
FIG. 4E shows representative BL images of A549 cell lysates obtained after cells were cultured in a 1% or 20% oxygen atmosphere for 2 days prior to incubation with BL660-NTR for 60 mins.
Figure 4F:
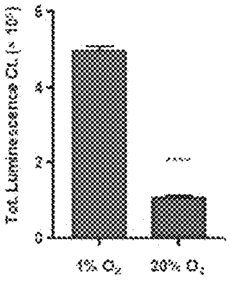
FIG. 4F is a bar graph of total luminescence count on a scale of $\times10^5$ quantified data from images of FIG. 4E, n=4, error bars=SEM, wherein statistical analysis was performed using a two-tailed t-test (α=0.05, **** P<0.001)
Figure 13:
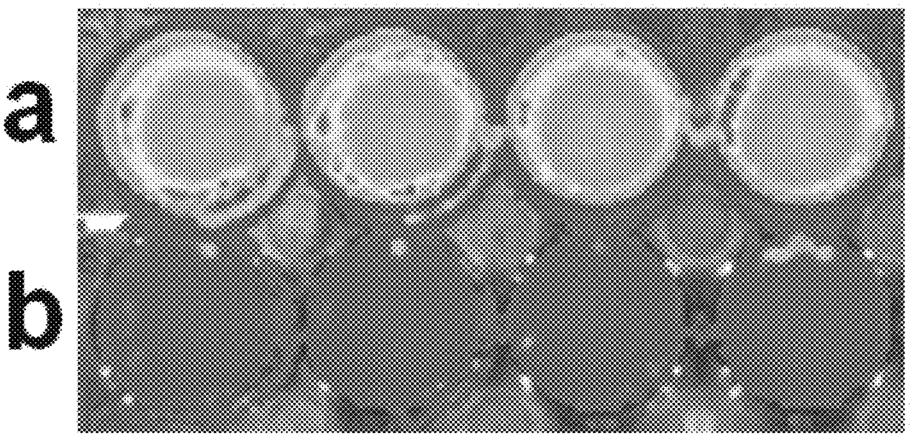
FIG. 13 shows BL images of A549 cell lysates obtained after cells were cultured in a 1% oxygen atmosphere (horizontal row 'a') or 20% oxygen atmosphere (row 'b') for 2 days prior to incubation with BL660-NTR for 60 mins.

Next, we performed a cell imaging study to measure hypoxia within a living system. Specifically, A549 cells (not expressing Luc) were cultured in an atmosphere consisting of 1% or 20% oxygen for 2 days to mimic hypoxic conditions (1%) or normoxic (20%), respectively. Because aryl nitro reduction mediated by mammalian NTRs can be inhibited by molecular oxygen, we expect there to be greater probe activation under oxygen-deficient conditions. After incubating with BL660-NTR for 60 minutes, the cells were washed with fresh PBS, detached, pelleted, and lysed via sonication. The lysates were then transferred to 24-well plates, treated with luciferase and imaged immediately using the IVIS imaging system. As shown in FIG. 4*e*, wells containing lysates obtained from the cells incubated under hypoxic conditions ($5.0\pm0.1\times10^5$ total luminescent counts) were significantly brighter than the corresponding normoxic lysates ($1.1\pm0.03\times10^5$ total luminescent counts) (FIG. 4*f* and FIG. 13). This represents a significant 4.5-fold difference in BL intensity.

In Vivo Application of BL660-NTR to Detect Tumor Hypoxia

Finally, we employed BL660-NTR in vivo to image tumor hypoxia (via NTR activity). Hypoxia is defined as a condition where the demand for oxygen from rapidly dividing cancer cells, outweigh the available supply. This condition emerges as the distance between the cancer cells and nutrient-rich blood vessels become greater as a function of tumor growth. Although it is estimated that ~50% of solid tumors are hypoxic, it is impossible to know whether a given lesion is oxygen-deficient without a reliable readout. This knowledge becomes critical when using luciferase-expressing cells to study cancer biology because hypoxia can strongly influence tumor properties (e.g., drug resistance, tumorigenesis, etc.). Of note, although several NTR probes for BL have been developed previously, BL660-NTR is the first example capable of deep-tissue detection of hypoxia via NIR BL imaging.

Figure 5A:
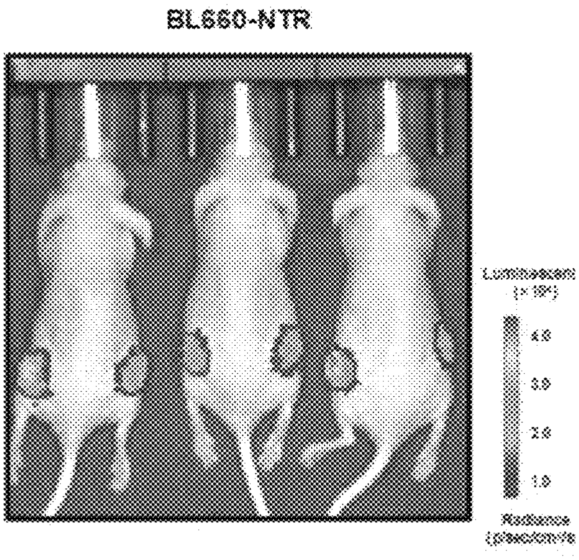
FIG. 5A is a bioluminescence image of NU/J mice bearing A549-Luc2 tumors acquired 15 mins after systemic administration of BL660-NTR.
Figure 5B:
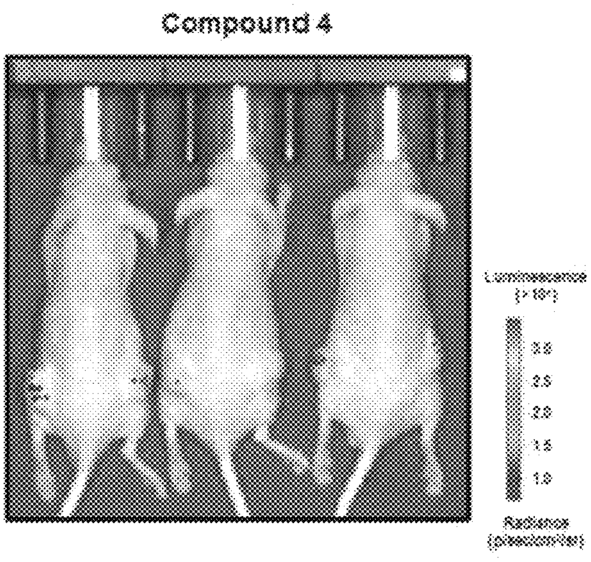
FIG. 5B is a bioluminescence image of NU/J mice bearing A549-Luc2 tumors acquired 15 mins after systemic administration of Compound (4)
Figure 5C:
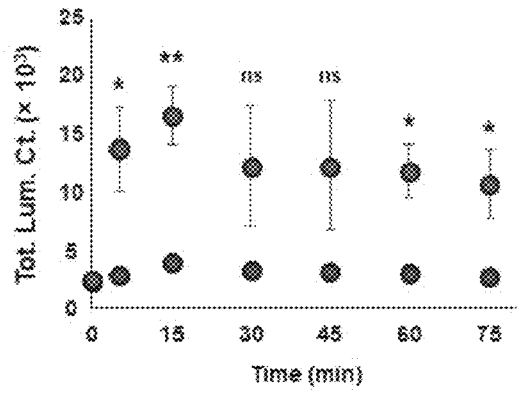
FIG. 5C is a graph of total luminescence count of animals treated with BL660-NTR (upper horizontal row, and the point at T=0) or Compound (4) (lower horizontal row). Data acquired at time=0 min (before injection) and at 5, 15, 30, 45, 60, and 75 min after injection (vertically scaled at $\times10^3$)
Figure 14:
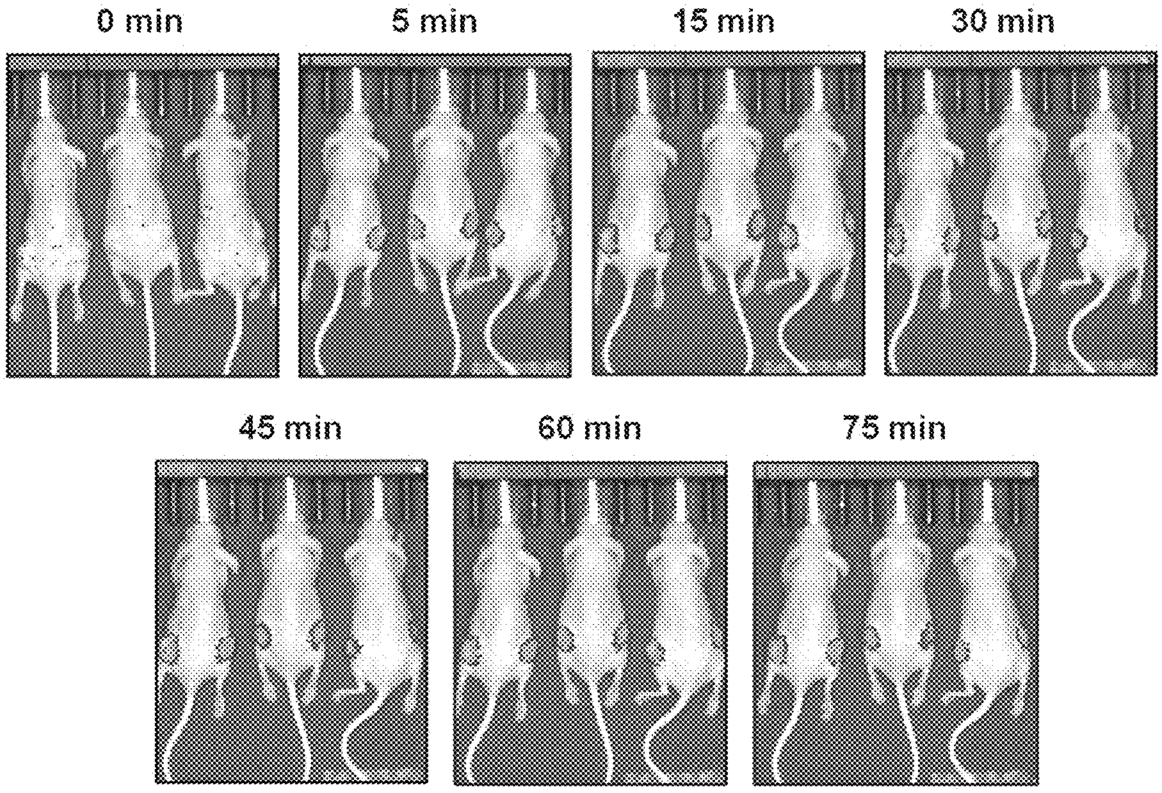
FIG. 14 is a series of BL images of NU/J mice bearing A549-Luc2 tumors acquired immediately before treatment and 5, 15, 30, 45, 60, and 75 mins after systemic administration of BL660-NTR as described in reference to FIG. 5A. Images were obtained in open mode.

NU/J mice (male, ~5-weeks old) were inoculated with A549-Luc2 lung cancer cells ($5\times10^6$) in both flanks. Testing of BL660-NTR commenced after tumors had grown to a volume of ~300 $mm^3$ (~4 weeks). First, we performed imaging using BL660-NTR, which was administered systemically via retroorbital injection (ROI) (FIG. 5*a* (upper horizontal row of points) and FIG. 14). ROIs were drawn around each tumor and the luminescent count was summed for each animal. By the first scan (5 min), strong BL signals were apparent in all tumors. The BL intensity appears to decrease slightly after 15 mins and levels off until the end of the experiment (75 mins) (FIG. 5*c*).

Figure 5D:
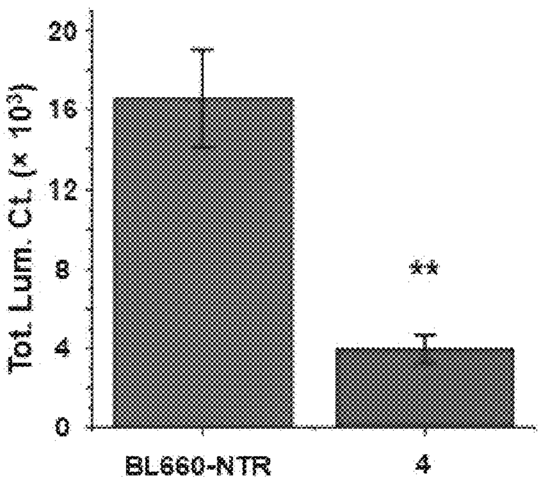
FIG. 5D is a bar graph of total luminescence count (vertically scaled at ×10 3) of imaging data from 15 min time point. n=3 for all experiments. Error bars=Standard deviation. Statistical analysis shown in FIG. 5C and FIG. 5D was performed using a two-tailed t-test (α=0.05, * P<0.05, ** P<0.01, ns=not significant)
Figure 6A:
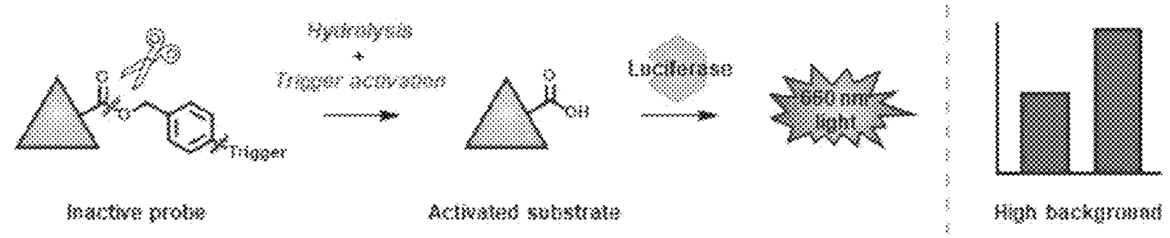
FIG. 6A PRIOR ART
FIG. 6A is a schematic illustration of how the use of prior art self-immolative linkers to install ABS triggers can lead to high background.
Figure 6B:
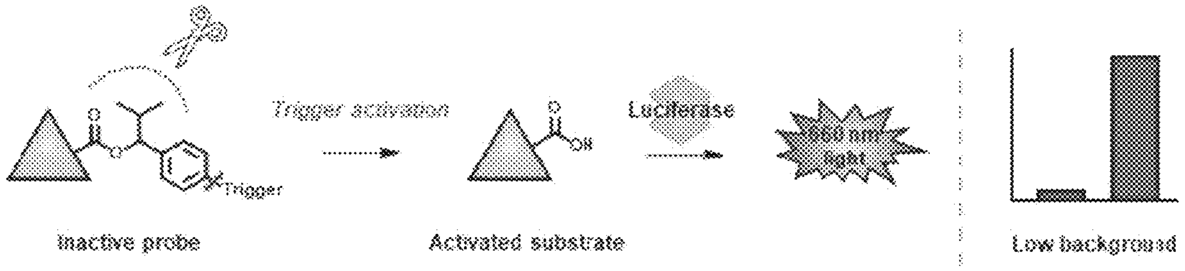
FIG. 6B is a schematic illustration of how the use of Linkers based on hydrolysis-resistant ester according to one embodiment ameliorates background in contrast to FIG. 6A.
Figures 15, 16:
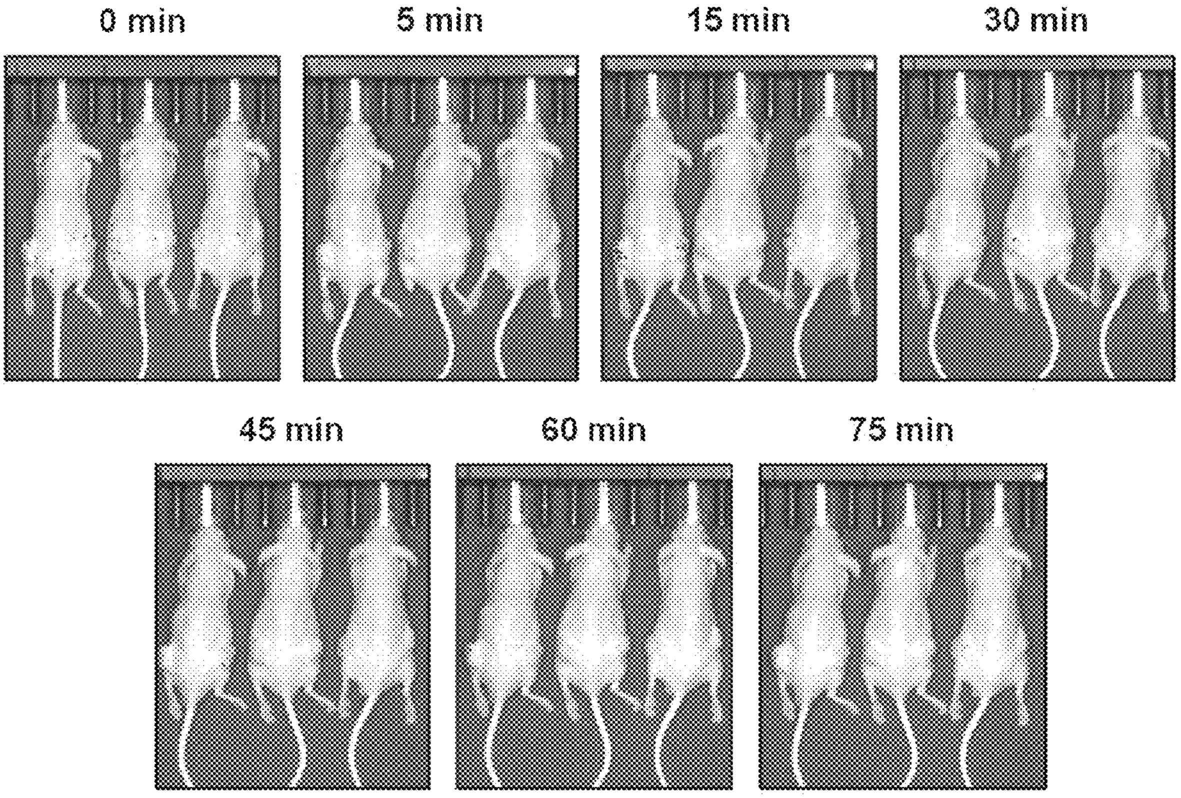
FIG. 15 is a series of BL images of NU/J mice bearing A549-Luc2 tumors acquired immediately before treatment and 5, 15, 30, 45, 60, and 75 mins after systemic administration of Compound (4). Images were obtained in open mode.
FIG. 16 is a table of normalized cell viable after treatment with the MTX protected esters. n=3

Next, to distinguish between NTR activation and off-target ester hydrolysis, we employed Compound (4) as a control reagent, which only differs in that the nitro trigger is absent (FIG. 1*a*). After approximately 20 hours, the same animals were treated with Compound (4) and imaged (FIG. 5*b* and FIG. 15). This delay was to ensure the probe had fully cleared from the first experiment. Despite dosing at the same concentration, the BL signal in the tumors at all time points were barely discernable from background (FIG. 5*c*). The total luminescent count after 15 mins for Compound 4 was only $4.0\pm0.7\times10^3$; whereas the corresponding readout was $16.6\pm2.5\times10^3$ for BL660-NTR. This represents a 5.2-fold difference, indicating successful detection of tumor hypoxia (FIG. 5*d*).

While the present disclosure can take many different forms, for the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Any alterations and further modifications of the described embodiments, and any further applications of the principles of the disclosure as described herein are contemplated as would normally occur to one skilled in the art to which the disclosure relates.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended aspects. The specific embodiments provided herein are examples of useful embodiments of the present disclosure and it will be apparent to one skilled in the art that the present disclosure may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this disclosure for a given application. In specific applications, the selection of a given anion or cation for preparation of a salt may result in increased or decreased solubility of that salt.

Every formulation or combination of components described or exemplified herein can be used to practice the disclosure, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein.

All patents and publications mentioned in the specification are indicative of the levels of skill of those skilled in the art to which the disclosure pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are disclosed, it should be understood that compounds known and available in the art prior to Applicant's disclosure, including compounds for which an enabling disclosure is provided in the references cited herein, are not intended to be included in the composition of matter aspects herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the disclosure without resort to undue experimentation. All art-known functional equivalents, of any such materials and methods are intended to be included in this disclosure. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended aspects.

EXAMPLES

Example 1

Synthesis of BL660-NTR

Preparation of 2-Methyl-1-(4-nitrophenyl)propan-1-ol (Referred to Herein as 'Compound (6)').

A solution of phenyllithium in dibutyl ether (1.9 M, 1.69 mL, 3.21 mmol, 1 equiv.) was slowly added to a cooled (−78° C.) solution of 4-nitro iodobenzene (0.8 g, 3.21 mmol, 1 equiv.) in anhydrous THF (16 mL) under N2. The reaction was stirred for 45 min at the same temperature to afford 5 in situ, then a solution of isobutyraldehyde (0.32 mL, 3.50 mmol, 1.1 equiv.) in anhydrous THF (3 mL) was added dropwise. The reaction was stirred for an additional one hour at −78° C. before warming to room temp. The reaction mixture was then quenched with saturated aqueous NH4Cl, transferred to a separatory funnel, and extracted with diethyl ether (3×). The combined organic layers were dried over Na2SO4, filtered, concentrated, and purified using silica gel column chromatography (eluent: 3:17 v/v EtOAc:Hexanes) to afford Compound (6) in 20% yield. (0.126 g, 0.64 mmol). 1H NMR (500 MHz, CDCl3) δ 8.20 (d, J=8.9 Hz, 2H), 7.49 (d, J=8.7 Hz, 2H), 4.56 (dd, J=6.1, 3.2 Hz, 1H), 2.01-1.94 (m, 2H), 0.95 (d, J=6.7 Hz, 3H), 0.87 (d, J=6.9 Hz, 3H). 13C NMR (126 MHz, CDCl3) δ 17.50, 19.01, 35.56, 78.81, 123.53, 127.41, 147.38, 151.05. HRMS [M+H]+ calculated mass for $C_{10}H_{14}NO_3$=196.09737, found=196.09733.

Preparation of BL660-NTR

A solution of BL660 (17.3 mg, 0.052 mmol, 1 equiv.) and pyridine (4.23 mL, 0.052 mmol, 1 equiv.) in anhydrous $CH_2C_{12}$ (1.5 mL) was cooled to −20° C. under the N2 atmosphere. Cyanuric fluoride (4.85 mL, 0.056 mmol, 1.08 equiv.) was slowly added to the reaction and stirred at the same temp. for ~40 min. A solution of Compound (6) (28.6 mg, 0.146 mmol, 2.8 equiv.) in anhydrous $CH_2C_{12}$ (0.5 mL) was added dropwise at the same temperature. The reaction was slowly brought to room temperature and was stirred for an additional 1.5 h at room temperature. After quenching with crushed ice, the organic layer was removed, and the aqueous layer was extracted with CH2C12. The combined organic layers were dried over Na2SO4, filtered, concentrated, and purified using silica gel column chromatography (eluent: 1:4 v/v EtOAc:Hexanes) to afford BL660-NTR in 10% yield (2.7 mg, 0.005 mmol). 1H NMR (400 MHz, CDCl3) δ 8.25-8.16 (m, 2H), 7.48 (d, J=8.7 Hz, 2H), 7.33 (d, J=8.5 Hz, 2H), 7.00-6.90 (m, 1H), 6.80-6.57 (m, 4H), 6.56-6.48 (m, 1H), 5.61 (d, J=6.7 Hz, 1H), 5.27-5.19 (m, 1H), 3.53 (t, J=8.3 Hz, 2H), 3.44-3.33 (m, 4H), 2.24-2.11 (m, 1H), 1.18 (t, J=7.1 Hz, 6H), 1.00 (d, J=6.7 Hz, 3H), 0.85 (d, J=3.5 Hz, 3H). HRMS [M+H]+ calculated mass for C28H34N3O4S=508.2270, found=508.2262.

Example 2

MTT Assay using MTX-Me2 and MTX-PhiPr2

48-well plates were seeded with 30,000 A549 cells per well (500 μL of 60,000 cells/mL) and incubated at 37° C. with 5% CO2 for 24 hours. Media was removed and fresh serum-free RPMI 1640 containing 0, 0.001, 0.01, 0.1, 1, 10 μL of MTX-Me2 or MTX-(PriPr)2 were added (0.1% DMSO final v/v). The media was removed after 24 hours incubation and replaced with 500 μL of a 20:1 mixture of serum-free RPMI 1640 and (3-(4,5-dimethylthiazol2-yl)-2, 5-diphenyl-tetrazolium bromide (MTT, 5 mg/mL stock in PBS). The cells were incubated for 2 hours under the same condition and then the medium was removed and replaced with DMSO (500 μL/well). The absorbance of each well was recorded at 555 nm on a microplate reader. Viability was calculated by the absorbance relative to the vehicle control.

Example 3

Detection of NTR Activity in A549 Lung Cancer Cells

A549 cells were seeded in T75 culture flasks and incubated in 1% or 20% oxygen atmosphere for 48 hours. A solution of BL660-NTR in DMSO (2 mM, 50 μL) was quickly added into each flask such that the final concentration of the probe is 10 μM and 0.5% DMSO. The cells were incubated with the probe for 60 minutes (under the respective culture conditions), washed with fresh PBS, and detached from the culture flasks. The cells were then transferred to a 15 mL centrifuge tube and pelleted at 1000 rpm for 5 min at room temp. The cells (4.25×106 cells/mL) were then resuspended in PBS along with 10% protease inhibitor solution (1 protease inhibitor mini tablet per 10 mL PBS, Pierce, Thermo Fisher Scientific) and sonicated on ice for 2.5 minutes (pulse 01, 01, 40%). The cell debris was removed via centrifugation at 4° C. The cell lysates were further diluted 2.5-fold by PBS and 475 μL were transferred into 24-well plates (n=4 for each condition), treated with luciferase (25 μL, 0.25 mg/mL), and imaged immediately using the IVIS imaging system. Bioluminescence light was collected in open mode (no filters were applied). ROIs were drawn around each well. The signal intensity was quantified using the Living Image Analysis Software.

Example 4

BL Imaging of Hypoxia in a Lung Cancer Model

NU/J mice bearing A549-Luc2 tumors were anesthetized using isoflurane (1-3% for maintenance; up to 5% for induction) in oxygen from a precision vaporizer. After testing to ensure animals are fully under anesthesia, an initial background scan is recorded. BL660-NTR or compound 4 formulated in 3:7 v/v DMSO:PBS. The solution was filtered through a 0.22 μM sterile filter immediately prior to use. The typical injection volume is ~100 μM at a dose of 2.2 μmol/kg. The solution was then administered via retroorbital injection. Images were captured using the IVIS® imaging system at 5, 15, 30, 45, 60, and 75 minutes after injection. Images at 15 minutes are shown in FIG. 5*a*. Bioluminescence light was collected in open mode (no filters were applied). Regions of interest ("ROIs") were drawn around each tumor and summed for each animal. The signal intensity was quantified using the Living Image Analysis Software and is represented in FIGS. 5*c* and 5*d*.

Example 5

Materials: Materials were purchased from commercial vendors and used without further purification. All deuterated solvents were purchased from Cambridge Isotope Laboratories. Isoamyl nitritel and triethyl 4-phosphonocrotonate were purchased from Acros Organic. Disodium ethylenediaminetetraacetate dihydrate (EDTA) was purchased from Alfa Aesar. QuantiLum® Recombinant Luciferase was purchased from Promega. CD68 Polyclonal antibody and Proteintech iNOS Polyclonal antibody were purchased from Thermo Fisher Scientific. Diethylammonium (Z)-1-(N,N-diethylamino)diazen-1-ium-1,2-diolate (DEA NONO ate), Fatty Acid Amide Hydrolase (human, recombinant), and Methyl beta-D-glucopyranoside were purchased from Cayman Chemical Company. Methotrexate was purchased from A2B Chem. Acetone, anhydrous dimethylformamide, dichloromethane, ethyl acetate, sodium bicarbonate, sodium chloride, sodium hydroxide were purchased from Thermo Fisher Scientific. Anhydrous methanol and hydrogen peroxide (30% v/v) were purchased from Macron Fine Chemicals. Concn. Hydrochloric acid and pentane were purchased from VMR BDH chemicals. Adenosine triphosphate magnesium salt, Ammonium iron(II) sulfate hexahydrate, Anhydrous acetonitrile, anhydrous dichloromethane, anhydrous tetrahydrofuran, benzhydrol, bromobenzene, sodium hydride, sodium hypochlorite, sodium sulfide nonahydrate, 4-(diethylamino)benzaldehyde, celite 545, chloroform, copper(II) chloride, dimethyl sulfoxide, esterase from porcine liver (lyophilized), fetal bovine serum (FBS), glutathione (reduced), hexane, 1-iodo-4-nitrobenzene, L-cysteine, lipase, nitroreductase, potassium superoxide, sec-phenethyl alcohol, tetrabromoethane, tetrakis(acetonitrile)copper(I) hexafluorophosphate, and triphenylphosphine oxide were purchased from Millipore-Sigma Aldrich. Caesium carbonate, D-cysteine-(S-Trityl)-OMe, 4-dimethylaminopyridine, 1-(3-Dimethylaminopropyl)-3-ethylcarbodiimide hydrochloride (EDC), trifluoromethanesulfonic anhydride, N,N'-diisopropylethylamine (DIPEA), isobutyraldehyde, magnesium metal, magnesium sulfate, potassium iodide, sodium sulfate (anhydrous), and triphenylphosphine were purchased from Oakwood Chemicals. Ammonium bicarbonate and isopropyl alcohol were purchased from Fischer Chemicals. Anhydrous ethanol was purchased from Decon Labs, Inc. Silver carbonate was purchased from AK scientific. Iodine was purchased from TCI America, Inc. Beta-Nicotinamide adenine dinucleotide, reduced disodium salt hydrate and 2-methyl-1-phenylpropan-1-ol were purchased from Combi-Blocks. Penicillin/streptomycin was purchased from Corning Inc. Human carboxylesterase 2 (hCES2) was purchased from Sino Biological Inc.

Example 6

Instruments and Software: $^1$H and $^{13}$C NMR spectra were acquired on a Varian 500 or Carver B500 spectrometer. The following abbreviations were used to describe coupling constants: singlet (s), doublet (d), triplet (t), quartet (q) or multiplet (m). Spectra were visualized and analyzed using MestReNova spectral data analyzing software (version 14.2) and referenced to trace non-deuterated solvent. High-resolution mass spectra were acquired on a Waters Q-TOF Ultima ESI mass spectrometer or a Waters Synapt G2-Si ESI/LC-MS spectrometer. MTT assays were analyzed using a SpectraMax M2 plate reader. BL images were acquired using an IVIS imaging system (PerkinElmer). Cells were visualized on an EVOS FL epifluorescence microscope and cellular imaging was performed using IVIS imaging system (PerkinElmer). A Countess® II FL Automated Cell Counter was used for cell viability assays. IVIS images were analyzed using Living Image Software PerkinElmer. Data were analyzed using Microsoft Excel and GraphPad Prism (version 6.0 or 8.0) and final figures were prepared in PowerPoint (version Microsoft 365).

Example 7

Synthetic Procedures: Thin-layer chromatography (TLC) was performed on glass-backed TLC plates precoated with silica gel containing an UV254 fluorescent indicator (Macherey-Nagel). TLCs were visualized with a 254/365 nm UV hand-held lamp (UVP). Flash silica gel chromatography was performed using 0.04-0.063 mm 60 M silica (Macherey-Nagel). All glassware used under anhydrous reaction conditions were flame-dried under vacuum and cooled immediately before use.

Example 8

Synthesis of Compound (1). To a solution of BL660 (23 mg, 0.070 mmol, 1 equiv.) in anhydrous DMF (2 mL) under $N_2$ was added benzyl bromide (9.93 mL, 0.083 mmol, 1.2 equiv.) followed by silver carbonate (11.5 mg, 0.042 mmol, 0.6 equiv.). The reaction mixture was stirred for 24 hours at room temperature and then quenched with saturated aqueous $NH_4Cl$. The reaction was transferred to a separatory funnel and extracted with EtOAc (3×). The combined organic layers were dried over $Na_2SO_4$, filtered, concentrated, and purified using silica gel column chromatography (eluent: 3:17 v/v EtOAc:Hexanes) to afford (1) in 50.2% yield. (15.2 mg, 0.036 mmol).

Example 9

Synthesis of Compound (2). A solution of BL660 (40.2 mg, 0.122 mmol, 1 equiv.) and pyridine (9.84 mL, 0.122 mmol, 1 equiv.) in anhydrous $CH_2C_{12}$ (2 mL) was cooled to −20° C. under a N2 atmosphere. Cyanuric fluoride (11.06 mL, 0.129 mmol, 1.06 equiv.) was slowly added to the reaction and stirred at the same temperature for ~40 minutes. A solution of benzhydrol (67.2 mg, 0.365 mmol, 3 equiv.) in anhydrous $CH_2C_{12}$ (0.5 mL) was added dropwise at the same temperature. The reaction was slowly brought to room temperature and was stirred for an additional 1.5 hours at room temperature. After quenching with cold brine, the organic layer was separated, and the aqueous layer was extracted with $CH_2C_{12}$ (3×). The combined organic layers were dried over $Na_2SO_4$, filtered, concentrated, and purified using silica gel column chromatography (eluent: 3:17 v/v EtOAc:Hexanes) to afford (2) in 10% yield (6 mg, 0.012 mmol).

Example 10

Synthesis of Compound (3). A solution of BL660 (40.2 mg, 0.122 mmol, 1 equiv.) and pyridine (9.84 mL, 0.122 mmol, 1 equiv.) in anhydrous $CH_2C_{12}$ (2 mL) was cooled to −20° C. under a $N_2$ atmosphere. Cyanuric fluoride (11.06 mL, 0.129 mmol, 1.06 equiv.) was slowly added to the reaction and stirred at the same temperature for ~40 min. A solution of 1-phenyl ethyl-1-ol (44.23 mL, 0.367 mmol, 3 equiv.) in anhydrous $CH_2C_{12}$ (0.5 mL) was added dropwise at the same temperature. The reaction was slowly brought to room temperature and was stirred for an additional 1.5 hours at room temperature. After quenching with cold brine, the organic layer was separated, and the aqueous layer was extracted with CH2C12 (3×). The combined organic layers were dried over $Na_2SO_4$, filtered, concentrated, and purified using silica gel column chromatography (eluent: 3:17 v/v EtOAc:Hexanes) to afford (3) in 23% yield (12 mg, 0.028 mmol).

Example 11

Synthesis of Compound (4). A solution of BL660 (40.2 mg, 0.122 mmol, 1 equiv.) and pyridine (9.84 mL, 0.122 mmol, 1 equiv.) in anhydrous $CH_2C_{12}$ (2 mL) was cooled to −20° C. under a N2 atmosphere. Cyanuric fluoride (11.06 mL, 0.129 mmol, 1.06 equiv.) was slowly added to the reaction and stirred at the same temperature for ~40 min. A solution of 1-phenyl 2-methyl-propane-1-ol (55.21 mL, 0.365 mmol, 3 equiv.) in anhydrous $CH_2C_{12}$ (0.5 mL) was added dropwise at the same temperature. The reaction was slowly brought to room temperature and was stirred for an additional 1.5 hours at room temperature. After quenching with cold brine, the organic layer was separated, and the aqueous layer was extracted with $CH_2C_{12}$ (3×). The combined organic layers were dried over $Na_2SO_4$, filtered, concentrated, and purified using silica gel column chromatography (eluent: 1:4 v/v EtOAc:Hexanes) to afford (4) in 14% yield (8 mg, 0.017 mmol).

Example 12

Assessment of Hydrolytic Stability for Compound (4)

Compound (4) (10 μM final concentration with 1% DMSO) was first incubated in Britton-Robinson buffer (pH 5, 7.4 and 9) at 37° C. for 2, 3 and 4 hrs. Then the pH's were adjusted to 7.4. Luminescence was measured by blocking excitation light and measuring emissions with 660 nm gating. Total volume of the reaction mixture was maintained at 100 μL. To the 50 μL of this reaction mixture was ATP-$MgSO_4$ (45 μL, prepared by mixing 17.78 mM ATP-Mg and 35.56 mM $MgSO_4$ in 1:1 ratio in PBS buffer) and the reaction was initiated with Luciferase (5 μL, 0.25 mg/mL in PBS containing 10% glycerol).

Example 13

Enzyme Selectivity Assay for Compound 4. The response of Compound 4 (5 μM) against a panel of enzymes known to possess ester-cleaving activity (porcine liver esterase, lipase, carboxyesterase, monoacylglycerol lipase, fatty acid amide hydrolase, and aldehyde dehydrogenase) was examined in a 96-well culture plate using the IVIS imaging system. Compound 4 was incubated with 10 mU of each enzyme at 37° C. for 30 min before ATP-$MgSO_4$ and luciferase were added to initiate bioluminescence production. Light was collected immediately after mixing, and the signal enhancement was determined relative to control wells not treated with enzyme. The total volume of each well was 100 μL (PBS (pH 7.4) with 0.5% DMSO). ALDH 1A1 was used at a final concentration of 100 nM. All other enzymes were prepared by dilution or dissolution from commercially available sources. All data is reported as the mean ±standard deviation (n=3).

Example 14

Analyte Selectivity Assay for BL660-NTR. The response of BL660-NTR (5 μM) toward a panel of biologically relevant metal ions, reactive oxygen species, reactive nitrogen species, and reactive sulfur species (50 equiv) in a 96-well culture plate was monitored using the IVIS imaging system. BL660-NTR was incubated with each analyte at 37° C. for 30 min before the reaction was initiated by adding ATP-$MgSO_4$ and luciferase. Light was collected within 15 min after mixing, and the signal enhancement was determined relative to control wells not treated with analyte. The total volume of each well was 100 μL [PBS (pH 7.4) with 0.5% DMSO]. Metal ion solutions were prepared by dissolving in MilliQ $H_2O$ before use. Superoxide anion was added as a solution of potassium superoxide in DMSO. Hydroxide radical was generated according to the previously reported literature. Similarly, peroxynitrite was prepared according to the reported literature. NO was generated in situ from a solution of DEA-NONOate in degassed PBS buffer. Glutathione reduced form was maintained at the final concentration of 5 mM in the reaction mixture. H2S was generated just before use according to the reported literature. NTR was used one unit per well. All other analytes were prepared by dilution or dissolution from commercially available sources.

Example 15

Dose-dependence Activation of BL660-NTR (FIG. 4*a*) by NTR: The response of BL660-NTR (5 μM) against different concentrations of NTR was measured in a 96-well culture plate and was monitored using the IVIS imaging system. BL660-NTR was incubated with either 0.01 U or 0.1 U NTR at 37° C. for 15 min before the wells were treated with ATP-$MgSO_4$ and luciferase to initiation bioluminescence production. Light was collected immediately after mixing, and the signal enhancement was determined relative to control wells not treated with enzyme. The total volume of each well was 100 μL (PBS (pH 7.4) with 0.5% DMSO). All data is reported as the mean±standard deviation (n=5).

Example 16

Cell Culture

4T1-Luc cell was cultured in phenol red-free RPMI 1640 (ATCC) with 10% fetal bovine serum (FBS, Sigma Aldrich), and 1% penicillin/streptomycin (Corning).

Example 17

Evaluation of BL660-Me and 4 in 4T1-Luc Cells. 4T1-Luc cells (180K) were seeded into 24-well plates and incubated for 24 hours. The cells were ~85% confluent. The media was removed and replaced with serum-free RPMI 1640. An initial background scan was recorded on an IVIS imaging system in open mode where no filters were applied. Cells were then treated with DMSO (2.5 μL, 0.5%), BL660-Me, or compound 4 in DMSO (10 μM final concentration). After 30 minutes incubation at 37° C., bioluminescence was collected. ROIs were drawn around each well. The total luminescence count for each well for a given condition was averaged. The signal intensity was quantified using the Living Image Analysis Software.

Example 18

MTT Cytotoxicity Assay. 24-well plates were seeded with 180,000 cells per well (500 μL of 360,000 cells/mL) and incubated at 37° C. with 5% $CO_2$ for 24 h (~70% confluent). Media was removed and fresh RPMI 1640 media with 10% FBS containing 0, 5, 10 or 20 μM BL660-NTR (1% DMSO final v/v) was added. The media was removed after 1 and 3 h and replaced with 500 μL of a 20:1 mixture of FBS-free RPMI 1640 and (3-(4,5-dimethylthiazol-2-yl)-2,5-diphenyltetrazolium bromide (MTT, 5 mg/mL stock in PBS). The cells were incubated for 2 h under the same conditions and then the medium was removed and replaced with DMSO (500 μL/well). The absorbance of each well was recorded after a 1:5 dilution in DMSO at 555 nm on a microplate reader. Viability was calculated by the absorbance relative to the vehicle control. Values are reported as the mean±standard deviation (n=3).

Example 19

Live-subject Statement. All animal experiments were performed with the approval of the Institutional Animal Care and Use Committee (IACUC) of the University of Illinois at Urbana—Champaign, following the principles outlined by the American Physiological Society on research animal use.

Example 20

Generation of a Subcutaneous Lung Cancer Model: A549 cells were treated with vehicle (media only) or 50 μM DETA NONOate in media for 10 days. Cells were washed with PBS, resuspended in serum-free media (Hams F-12K), and mixed 1:1 with Geltrex (v/v) (to a final concentration of 5×107 cells/mL). Tumors were generated by subcutaneously injecting 100 μL of these cell solutions into the flanks of 4-week-old Nu/J mice (The Jackson Laboratory stock #: 002019).

Example 21

Formulation of BL660-NTR or Compound 4 for In Vivo Imaging

BL660-NTR was dissolved in DMSO and diluted with PBS (3:7 v/v DMSO:PBS). The solution was filtered through a 0.22 μM sterile filter immediately prior to use. The typical injection volume is ~100 μM at a dose of 2.2 μmol/kg.

Compound 4 was dissolved in DMSO and diluted with PBS (3:7 v/v DMSO:PBS). The solution was filtered through a 0.22 μM sterile filter immediately prior to use. The typical injection volume is ~100 μM at a dose of 2.2 μmol/kg.

* Prior to formulation, stock solutions of BL660-NTR and compound 4 in DMSO (2 mM) was diluted and analyzed via UV-VIS-NIR spectrophotometry to ensure the concentrations were matched (up to 10% variability is considered acceptable).

The drug, markers and probes described herein can be administered in humans in the same ways as their respective prior art counterparts.

ABBREVIATIONS

DMSO=dimethyl sulfoxide. GFP=green fluorescent protein; HRMS=High resolution mass spectrometry. IC50=half maximal inhibitory concentration. mM=millimolar. mU=milliunit. MS=mass spectrometry. MTT=3-(4,5-dimethylthiazol-2-yl)-2,5-diphenyltetrazolium bromide. NIR=near-infrared. NMR=nuclear magnetic resonance. PBS=phosphate-buffered saline. ROI=region of interest. rpm=rotations per minute. SEM=standard error of the mean. SN1=unimolecular nucleophilic substitution. THF=tetrahydrofuran.

Although the present disclosure has been described with reference to certain embodiments thereof, other embodiments are possible without departing from the present disclosure. The spirit and scope of the appended aspects should not be limited, therefore, to the description of the preferred embodiments contained herein. All embodiments that come within the meaning of the aspects, either literally or by equivalence, are intended to be embraced therein. Furthermore, the advantages described above are not necessarily the only advantages of the disclosure, and it is not necessarily expected that all of the described advantages will be achieved with every embodiment of the disclosure.

What is claimed is:

1. A compound of the formula:

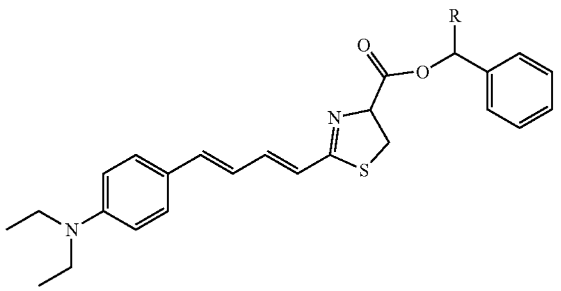

wherein R is selected from the group consisting of —H, methyl, phenyl, isopropyl, isobutyl and isopentyl.

2. The compound of claim 1 wherein R is a phenyl group.

3. The compound of claim 1 wherein R is an isopropyl group.

4. A method of imaging mammalian cells, comprising: inoculating the mammal with a compound in accordance with claim 3, and measuring luminescence intensities.

5. The method of claim 4 wherein the phenyl group adjacent to R in the compound includes an —$NO_2$ group.

* * * * *